(12) United States Patent
Lin et al.

(10) Patent No.: US 8,658,160 B1
(45) Date of Patent: Feb. 25, 2014

(54) COMPOSITION AND METHOD FOR CANCER CHEMOPREVENTION

(75) Inventors: Henry John Lin, Palos Verdes Estates, CA (US); Brigette L. Tippin, Torrance, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 824 days.

(21) Appl. No.: 11/873,273

(22) Filed: Oct. 16, 2007

Related U.S. Application Data

(60) Provisional application No. 60/829,859, filed on Oct. 17, 2006.

(51) Int. Cl.
*A61K 38/43* (2006.01)
*A61K 38/00* (2006.01)
*C12N 9/00* (2006.01)
*C12N 9/90* (2006.01)
*C07K 17/00* (2006.01)

(52) U.S. Cl.
USPC ......... 424/94.1; 424/94.5; 435/183; 435/233; 530/350

(58) Field of Classification Search
None
See application file for complete search history.

(56) References Cited

U.S. PATENT DOCUMENTS

| | | |
|---|---|---|
| 5,693,671 A | 12/1997 | Niihara et al. |
| 6,080,428 A | 6/2000 | Bova |
| 6,129,930 A | 10/2000 | Bova |
| 6,406,715 B1 | 6/2002 | Cefali |
| 6,495,537 B1 | 12/2002 | Jacobson et al. |
| 6,676,967 B1 | 1/2004 | Cefali et al. |
| 6,746,691 B2 | 6/2004 | Cefali |
| 6,818,229 B1 | 11/2004 | Cefali et al. |

OTHER PUBLICATIONS

Chica et al. Curr Opin Biotechnol. Aug. 2005;16(4):378-84.*
Akiyama, et al., "Conditional Disruption of the Peroxisome Proliferator-Activated Receptor γ Gene in Mice Results in Lowered Expression of ABCA1, ABCG1, and apoE in Macrophages and Reduced Cholesterol Efflux," Molecular and Cellular Biology, Apr. 2002, pp. 2607-2619, vol. 22(8).
Bell-Parikh, et al., "Biosynthesis of 15-deoxy-$\Delta^{12,14}$ -$PGJ_2$ and the ligation of PPARγ," J. Clin. Invest., Sep. 2003, pp. 945-955, vol. 112(6).
Benyo, et al., "GPR109A (PUMA-G/HM74A) mediates nicotinic acid-induced flushing," J. Clin. Invest., Dec. 2005, pp. 3634-3640, vol. 115(12).
Brockman, et al., "Activation of PPARγ Leads to Inhibition of Anchorage-Independent Growth of Human Colorectal Cancer Cells," Gastroenterology, 1998, pp. 1049-1055, vol. 115.
Chan, A., "Aspirin, non-steroidal anti-inflammatory drugs and colorectal neoplasia: future challenges in chemoprevention," Cancer Causes and Control, 2003, pp. 413-418, vol. 14.
Cheng, et al., "Antagonism of the prostaglandin $D_2$ receptor 1 suppresses nicotinic acid-induced vasodilation in mice and humans," Proc. Natl. Acad. Sci. USA, Apr. 25, 2006, pp. 6682-6687, vol. 103(17).
Eguchi, et al., "Lack of tactile pain (allodynia) in lipocalin-type prostaglandin D synthase-deficient mice," Proc. Natl. Acad. Sci. USA, Jan. 1999, pp. 726-730, vol. 96.
Fajas, et al., "The Organization, Promoter Analysis, and Expression of the Human PPARγ Gene," The Journal of Biological Chemistry, Jul. 25, 1997, pp. 18779-18789, vol. 272(30).
Fitzpatrick, et al., "Albumin-catalyzed Metabolism of Prostaglandin $D_2$," The Journal of Biological Chemistry, Oct. 10, 1983, pp. 11713-11718, vol. 258(19).
Forman, et al., "15-Deoxy-$\Delta^{12,14}$-Prostaglandin $J_2$ Is a Ligand for the Adipocyte Determination Factor PPARγ," Cell, Dec. 1, 1995, pp. 803-812, vol. 83.
Frazier, et al., "Cost-effectiveness of Screening for Colorectal Cancer in the General Population," JAMA, Oct. 18, 2000, pp. 1954-1961, vol. 284(15).
Fujitani, et al., "Pronounced Eosinophilic Lung Inflammation and Th2 Cytokine Release in Human Lipocalin-Type Prostaglandin D Synthase Transgenic Mice," The Journal of Immunology, 2002, pp. 443-449, vol. 168.
Fukushima, et al., "9-Deoxy-$\Delta^9$-Prostaglandin $D_2$, A Prostaglandin $D_2$ Derivative with Potent Antineoplastic and Weak Smooth Muscle-Contracting Activities," Biochemical and Biophysical Research Communications, Dec. 15, 1982, pp. 626-633, vol. 109(3).
Ganguly, et al., Conformation-sensitive gel electrophoresis for rapid detection of single-base differences in double-stranded PCR products and DNA fragments: Evidence for solvent-induced bends in DNA heteroduplexes, Proc. Natl. Acad. Sci. USA, Nov. 1993, pp. 10325-10329, vol. 90.

(Continued)

*Primary Examiner* — Christian Fronda
(74) *Attorney, Agent, or Firm* — Blakely Sokoloff Taylor & Zafman LLP

(57) ABSTRACT

A composition including an effective amount of a treatment agent to inhibit tumor growth in a mammal by manipulating a prostaglandin $D_2$ biosynthetic pathway. A method comprising introducing an effective amount of a treatment agent to a mammal to inhibit tumor growth by manipulating a prostaglandin $D_2$ biosynthetic pathway while at the same time reducing production of other forms of prostaglandins that may produce ill effects, such as prostaglandin $E_2$. A method comprising introducing an effective amount of a treatment agent to a mammal to inhibit tumor growth by manipulating a prostaglandin $D_2$ biosynthetic pathway while at the same time reducing potential undesirable side effects related to increased levels of prostaglandin $D_2$. A composition comprising a genetic variant of human hematopoietic prostaglandin D synthase (H-PGDS). A method comprising identifying an individual who carries a Val187Ile gene variant or allele and assessing a predisposition of an individual to various conditions.

8 Claims, 10 Drawing Sheets

(56) References Cited

OTHER PUBLICATIONS

Ghisletti, et al., "Parallel SUMOylation-Dependent Pathways Mediate Gene- and Signal-Specific Transrepression by LXRs and PPARγ," Molecular Cell, Jan. 12, 2007, pp. 57-70, vol. 25.
Girnun, et al., "APC-dependent suppression of colon carcinogenesis by PPARγ," Proc. Natl. Acad. Sci. USA, Oct. 15, 2002, pp. 13771-13776, vol. 99(21).
Goldberg, et al., "Multiple-Dose Efficacy and Safety of an Extended-Release Form of Niacin in the Management of Hyperlipidemia," Am. J. Cardiol., May 1, 2000, pp. 1100-1105, vol. 85.
Goodlad, et al., "Inhibiting vascular endothelial growth factor receptor-2 signaling reduces tumor burden in the $Apc^{min/+}$ mouse model of early intestinal cancer," Carcinogenesis, 2006, pp. 2133-2139, vol. 27(10).
Gross, et al., "Levels of Prostaglandin E Metabolite, the Major Urinary Metabolite of Prostaglandin $E_2$, Are Increased in Smokers," Clin. Cancer Res., Aug. 15, 2005, pp. 6087-6093, vol. 11(16).
Grundy, et al., "Efficacy, Safety, and Tolerability of Once-Daily Niacin for the Treatment of Dyslipidemia Associated With Type 2 Diabetes," Arch. Intern. Med., 2002, pp. 1568-1576, vol. 162.
Guerrero, et al., "Synthesis and Pharmacological Evaluation of a Selected Library of New Potential Anti-inflammatory Agents Bearing the γ-Hydroxybutenolide Scaffold: a New Class of Inhibitors of Prostanoid Production through the Selective Modulation of Microsomal Prostaglandin E Synthase-1 Expression," J. Med. Chem., 2007, pp. 2176-2184, vol. 50.
Guyton, et al., "Effectiveness of Once-Nightly Dosing of Extended-Release Niacin Alone and in Combination for Hypercholesterolemia," Am. J. Cardiol., Sep. 15, 1998, pp. 737-743, vol. 82.
Hirai, et al., "Prostaglandin D2 Selectively Induces Chemotaxis in T Helper Type 2 Cells, Eosinophils, and Basophils via Seven-Transmembrane Receptor CRTH2," J. Exp. Med., Jan. 15, 2001, pp. 255-261, vol. 193(2).
Hirata, et al., "Occurrence of 9-Deoxy-$\Delta^9$, $\Delta^{12}$-13,14-dihydroprostaglandin $D_2$ in Human Urine," The Journal of Biological Chemistry, Nov. 15, 1988, pp. 16619-16625, vol. 263(32).
Imperiale, et al., "Results of Screening Colonoscopy Among Persons 40 to 49 Years of Age," N. Engl. J. Med., Jun. 6, 2002, pp. 1781-1785, vol. 346(23).
Jones, et al., "Elimination of the non-specific binding of avidin to tissue sections," Histochemical Journal, 1987, pp. 264-268, vol. 19.
Kato, et al., "Antitumor Activity of $\Delta^7$-Prostaglandin $A_1$ and $\Delta^{12}$-Prostaglandin $J_2$ in Vitro and in Vivo," Cancer Research, Jul. 1986, pp. 3538-3542, vol. 46.
Kim, et al., "Suppression of Prostate Tumor Cell Growth by Stromal Cell Prostaglandin D Synthase-Derived Products," Cancer Res., Jul. 15, 2005, pp. 6189-6198, vol. 65(14).
Kliewer, et al., "A Prostaglandin $J_2$ Metabolite Binds Peroxisome Proliferator-Activated Receptor γ and Promotes Adipocyte Differentiation," Cell, Dec. 1, 1995, pp. 813-819, vol. 83.
Lakso, et al., "Efficient in vivo manipulation of mouse genomic sequences at the zygote stage," Proc. Natl. Acad. Sci. USA, Jun. 1996, pp. 5860-5865, vol. 93.
Lefebvre, et al., "Activation of the peroxisome proliferator-activated receptor γ promotes the development of colon tumors in C57BL/6J-$APC^{min}/+$ mice," Nature Medicine, Sep. 1998, pp. 1053-1057, vol. 4(9).
Lehmann, et al., "An Antidiabetic Thiazolidinedione Is a High Affinity Ligand for Peroxisome Proliferator-activated Receptor γ (PPARγ)," The Journal of Biological Chemistry, Jun. 2, 1995, pp. 12953-12956, vol. 270(22).
Li, et al., "RasGRP4 Regulates the Expression of Prostaglandin $D_2$ in Human and Rat Mast Cell Lines," The Journal of Biological Chemistry, Feb. 14, 2003, pp. 4725-4729, vol. 278(7).
Lin, et al., "Variants of N-acetyltransferase NAT1 and a case-control study of colorectal adenomas," Pharmacogenetics, 1998, pp. 269-281, vol. 8.

Mansen, et al., "Expression of the Peroxisome Proliferator-Activated Receptor (PPAR) in the Mouse Colonic Mucosa," Biochemical and Biophysical Research Communications, 1996, pp. 844-851, vol. 222.
Moon, et al., Curcumin Suppresses Interleukin 1β-Mediated Microsomal Prostaglandin E Synthase 1 by Altering Early Growth Response Gene 1 and Other Signaling Pathways, The Journal of Pharmacology and Experimental Therapeutics, 2005, pp. 788-795, vol. 315(2).
Morrow, et al., "Identification of Skin as a Major Site of Prostaglandin $D_2$ Release Following Oral Administration of Niacin in Humans," J. Invest. Dermatol., 1992, pp. 812-815, vol. 98.
Morrow, et al., "Release of Markedly Increased Quantities of Prostaglandin D2 in Vivo in Humans Following the Administration of Nicotinic Acid," Prostaglandins, Aug. 1989, pp. 263-274, vol. 38(2).
Narumiya, et al., "Site and Mechanism of Growth Inhibition by Prostaglandins. III. Distribution and Binding of Prostaglandin $A_2$ and $\Delta^{12}$-Prostaglandin $J_2$ in Nuclei," The Journal of Pharmacology and Experimental Therapeutics, 1987, pp. 306-311, vol. 242(1).
Ohshima, et al., "Transcriptional Activity of Peroxisome Proliferator-activated Receptor γ Is Modulated by SUMO-1 Modification," The Journal of Biological Chemistry, Jul. 9, 2004, pp. 29551-29557, vol. 279(28).
Oshima, et al., "Hyperplastic gastric tumors induced by activated macrophages in COX-2/mPGES-1 transgenic mice," The EMBO Journal, 2004, pp. 1669-1678, vol. 23.
O'Sullivan, et al., "Analyses of prostaglandin $D_2$ metabolites in urine: Comparison between enzyme immunoassay and negative ion chemical ionization gas chromatography-mass spectrometry," Prostaglandins & Other Lipid Mediators, 1999, pp. 149-165, vol. 57.
Park, et al., "Hematopoietic Prostaglandin D Synthase Suppresses Intestinal Adenomas in $Apc^{min/+}$ Mice," Cancer Res., Feb. 1, 2007, pp. 881-889, vol. 67(3).
Pascual, et al., "A SUMOylation-dependent pathway mediates transrepression of inflammatory response genes by PPAR-γ," Nature, Sep. 29, 2005, pp. 759-763, vol. 437.
Pinzar, et al., "Structural Basis of Hematopoietic Prostaglandin D Synthase Activity Elucidated by Site-directed Mutagenesis," The Journal of Biological Chemistry, Oct. 6, 2000, pp. 31239-31244, vol. 275(40).
Pinzar, et al., "Prostaglandin D synthase gene is involved in the regulation of non-rapid eye movement sleep," Proc. Natl. Acad. Sci. USA, Apr. 25, 2000, pp. 4903-4907, vol. 97(9).
Richman, et al., "Nicotinic Acid Receptor Agonists Differentially Activate Downstream Effectors," The Journal of Biological Chemistry, Jun. 22, 2007, pp. 18028-18036, vol. 282(25).
Ricote, et al., "PPARs and molecular mechanisms of transrepression," Biochimica et Biophysica Acta, 2007, pp. 926-935, vol. 1771.
Ricote, et al., The peroxisome proliferator-activated receptor-γ is a negative regulator of macrophage activation, Nature, Jan. 1, 1998, pp. 79-82, vol. 391.
Riendeau, et al., "Inhibitors of the inducible microsomal prostaglandin $E_2$ synthase (mPGES-1) derived from MK-886," Bioorganic & Medicinal Chemistry Letters, 2005, pp. 3352-3355, vol. 15.
Saez, et al., "Activators of the nuclear receptor PPARγ enhance colon polyp formation," Nature Medicine, Sep. 1998, pp. 1058-1061, vol. 4(9).
Sansom, et al., "*Myc* deletion rescues Apc deficiency in the small intestine," Nature, Apr. 5, 2007, pp. 676-679, vol. 446.
Sarraf, et al., "Loss-of-Function Mutations in PPARγ Associated with Human Colon Cancer," Molecular Cell, Jun. 1999, pp. 799-804, vol. 3.
Shibata, et al., "15-Deoxy-$\Delta^{12,14}$-Prostaglandin $J_2$," The Journal of Biological Chemistry, Mar. 22, 2002, pp. 10459-10466, vol. 277(12).
Straus, et al., "15-Deoxy-$\Delta^{12,14}$-prostaglandin $J_2$ inhibits multiple steps in the NF-κB signaling pathway," Proc. Natl. Acad. Sci. USA, Apr. 25, 2000, pp. 4844-4849, vol. 97(9).
Stringfellow, et al., "Prostaglandin $D_2$ controls pulmonary metastasis of malignant melanoma cells," Nature, Nov. 1, 1979, pp. 76-78, vol. 282.
Su, et al., "Multiple Intestinal Neoplasia Caused by a Mutation in the Murine Homolog of the APC Gene," Science, May 1, 1992, pp. 668-670, vol. 256.

(56) References Cited

OTHER PUBLICATIONS

Tang, et al., "Enhancement of arachidonic acid signaling pathway by nicotinic acid receptor HM74A," Biochemical and Biophysical Research Communications, 2006, pp. 29-37, vol. 345.
Terry, et al., "Association of Frequency and Duration of Aspirin Use and Hormone Receptor Status With Breast Cancer Risk," JAMA, May 26, 2004, pp. 2433-2440, vol. 291(20).
Tontonoz, et al., "mPPARγ2: tissue-specific regulator of an adipocyte enhancer," Genes & Development, 1994, pp. 1224-1234, vol. 8.
Trebino, et al., "Redirection of Eicosanoid Metabolism in MPGES-1-deficient Macrophages," The Journal of Biological Chemistry, Apr. 29, 2005, pp. 16579-16585, vol. 280(17).
Welch, et al., "PPARγ and PPARδ negatively regulate specific subsets of lipopolysaccharide and IFN-γ target genes in macrophages," Proc. Natl. Acad. Sci. USA, May 27, 2003, pp. 6712-6717, vol. 100(11).
Williams, et al., "Three new point mutations in type II procollagen (COL2A1) and identification of a fourth family with the COL2A1 Arg519→Cys base substitution using conformation sensitive gel electrophoresis," Human Molecular Genetics, 1995, pp. 309-312, vol. 4(2).
Yu, et al., "Nrf2-mediated Induction of Cytoprotective Enzymes by 15-Deoxy-$\Delta^{12,14}$-Prostaglandin $J_2$ Is Attenuated by Alkenal/one Oxidoreductase," The Journal of Biological Chemistry, Sep. 8, 2006, pp. 26245-26252, vol. 281(36).
Zhu, et al., "Cloning of a New Member of the Peroxisome Proliferator-activated Receptor gene Family from Mouse Liver," The Journal of Biological Chemistry, Dec. 25, 1993, pp. 26817-26820, vol. 268(36).
Zielinski, S., "Despite Positive Studies, Popularity of Chemoprevention Drugs Increasing Slowly," Journal of the National Cancer Institute, Oct. 6, 2004, pp, 1410-1412, vol. 96(19).
"NIASPAN® niacin extended-release tablets," http://www.niaspan.com, Mar. 2004, Kos Pharmaceuticals, Inc.
Jowsey, I.R., et al., "Mammalian class Sigma glutathione S-transferases; catalytic properties and tissue-specific expression of human and rat GSH-dependent prostaglandin $D_2$ synthases," Biochem. J., vol. 359 (2001) pp. 507-516.
Beljaars, L. et al., "Characteristics of the hepatic stellate cell-selective carrier mannose 6-phosphate modified albumin (M6P$_{28}$-HSA)", Liver, 21, (2001), 320-328.
Brown, W. J., et al., "Phospholipase $A_2$ ($PLA_2$) enzymes in membrane trafficking: mediators of membrane shape and function". Traffic, 4, (2003), 214-221.
Gelman, M. S., et al., "Identification of cell surface and secreted proteins essential for tumor cell survival using a genetic suppressor element screen", Oncogene, 23, (2004), 8158-8170.
Grewal, S., et al., "Cytosolic phospholipase $A_{2-\alpha}$ and cyclooxygenase-2 localize to intracellular membranes of EA.hy.926 endothelial cells that are distinct from the endoplasmic reticulum and the Golgi apparatus", FEBS Journal, 272, (2005), 1278-1290.
Grubb, J. H., et al., "New strategies for enzyme replacement therapy for lysosomal storage diseases", Rejuvenation Research, vol. 13, No. 2, (2010), 1-8.
Jovic, M., et al., "The early endosome: a busy sorting station for proteins at the crossroads", Histol Histopathol, 25, (2010), 99-112.
Lebowitz, J. H., et al., "Glycosylation-independent targeting enhances enzyme delivery to lysosomes and decreases storage in mucopolysaccharidosis type VII mice", PNAS, vol. 101, No. 9, (Mar. 2, 2004), 3083-3088.
Reggi, S., et al., "Recombinant human acid β-glucosidase stored in tobacco seed is stable, active and taken up by human fibroblasts", Plant Molecular Biology, 57, (2005), 101-113.
Sinclair, G., et al., "Secretion of human glucocerebrosidase from stable transformed insect cells using native signal sequences", Biochem. Cell Biol., 84, (2006), 148-156.
Sklar, M. M., et al., "Developmental expression of the tissue insulin-like growth factor II/mannose 6-phosphate receptor in the rat", The Journal of Biological Chemistry, vol. 264, No. 28, (1989), 16733-16738.
Terasawa, H., et al., "Solution structure of human insulin-like growth factor II; recognition sties for receptors and binding proteins", The EMBO Journal, vol. 13, No. 23, (1994), 5590-5597.
Urade, Y., et al., "Lipocalin-type and hematopoietic prostaglandin D syntases as a novel example of functional convergence", Prostaglandins & Other Lipid Mediators, 68-69, (2002), 375-382.
Walsh, G., "Biopharmaceutical benchmarks 2006", Nature Biotechnology, vol. 24, No. 7, (Jul. 2006), 769-776.
Wang, D., et al., "Pro-inflammatory prostaglandins and progression of colorectal cancer", Cancer Letters, 267, (2008), 197-203.
Winkel, L. P., et al., "Enzyme replacement therapy in late-onset pompe's disease: a three-year follow-up", American Neurological Association, 55, (2004), 495-502.
Kanaoka, Yoshihide, et al., "Cloning and Crystal Structure of Hematopoietic Prostaglandin D Synthase", *Cell*, vol. 90, (Sep. 19, 1997), 1085-1095.
Kanaoka, Yoshihide, et al., "Hematopoietic prostaglandin D synthase", *Prostaglandins, Leukotrienes and Essential Fatty Acids*, vol. 69, (2003), 163-167.
Kanaoka, Yoshihide, et al., "Structure and chromosomal localization of human and mouse genes for hematopoietic prostaglandin D synthase", *Eur. J. Biochem.*, vol. 267, (2000), 3315-3322.

\* cited by examiner

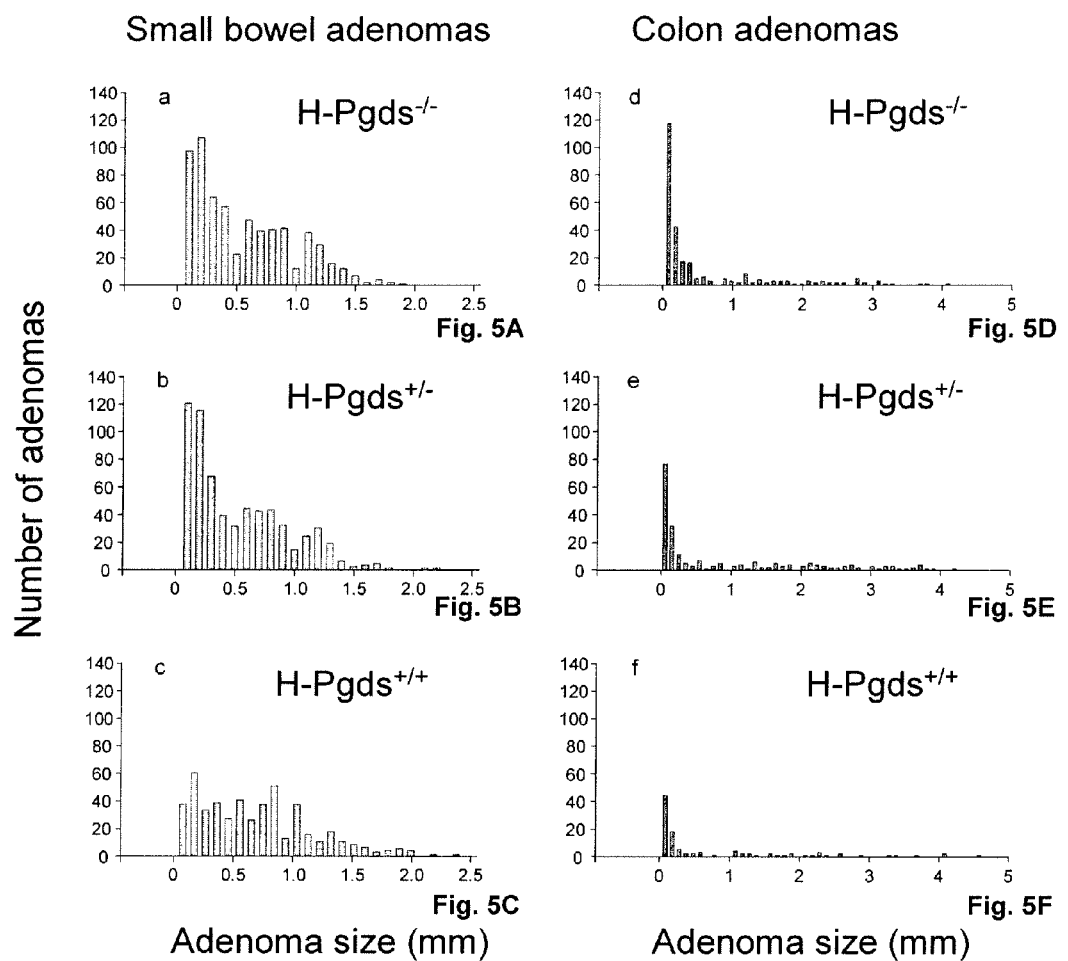

SEQUENCE LISTING

```
<160> NUMBER OF SEQ ID NOS: 1

<210> SEQ ID NO 1
<211> LENGTH: 199
<212> TYPE: PRT
<213> ORGANISM: Homo sapiens

<400> SEQUENCE: 1

Met Pro Asn Tyr Lys Leu Thr Tyr Phe Asn Met Arg Gly Arg Ala Glu
1               5                   10                  15

Ile Ile Arg Tyr Ile Phe Ala Tyr Leu Asp Ile Gln Tyr Glu Asp His
            20                  25                  30

Arg Ile Glu Gln Ala Asp Trp Pro Glu Ile Lys Ser Thr Leu Pro Phe
        35                  40                  45

Gly Lys Ile Pro Ile Leu Glu Val Asp Gly Leu Thr Leu His Gln Ser
    50                  55                  60

Leu Ala Ile Ala Arg Tyr Leu Thr Lys Asp Thr Asp Leu Ala Gly Asp
65                  70                  75                  80

Thr Glu Met Glu Gln Cys His Val Asp Ala Ile Val Asp Thr Leu Asp
                85                  90                  95

Asp Phe Met Ser Cys Phe Pro Trp Ala Glu Lys Lys Gln Asp Val Lys
            100                 105                 110

Glu Gln Met Phe Asp Glu Leu Leu Thr Tyr Asn Ala Pro His Leu Met
        115                 120                 125

Gln Asp Leu Asp Thr Tyr Leu Gly Gly Arg Glu Trp Leu Ile Gly Asn
    130                 135                 140

Ser Val Thr Trp Ala Asp Phe Tyr Trp Glu Ile Cys Ser Thr Thr Leu
145                 150                 155                 160

Leu Val Phe Lys Pro Asp Leu Leu Asp Asn His Pro Arg Leu Val Thr
                165                 170                 175

Leu Arg Lys Lys Val Gln Ala Ile Pro Ala Val Ala Asn Trp Ile Lys
            180                 185                 190

Arg Arg Pro Gln Thr Lys Leu
        195
```

COMPOSITION AND METHOD FOR CANCER CHEMOPREVENTION

CROSS REFERENCE TO RELATED APPLICATIONS

This application claims priority from U.S. Provisional Application Ser. No. 60/829,859, filed on Oct. 17, 2006, which is incorporated herein by reference in its entirety.

BACKGROUND

1. Field

Methods and compositions for cancer chemoprevention. In particular, methods and compositions that inhibit growth and/or development of tumors.

2. Background

Prostaglandins are members of a group of lipid compounds derived enzymatically from fatty acids and are found in nearly all tissues and organs. Prostaglandin $D_2$ ($PGD_2$) represents one group of prostaglandins, which are produced in the body by enzymes called prostaglandin D synthases.

Two enzymes account for $PGD_2$ production in the body. One enzyme is the brain type, which occurs in the nervous system, epididymis, and heart. It resembles lipophilic ligand-carrier proteins and is called lipocalin-type prostaglandin D synthase (L-PGDS). The enzyme is a β-barrel monomer that undergoes cleavage of a signal peptide, glycosylation, phosphorylation, and cysteine oxidation. Mice lacking L-PGDS do not have the normal pain response (allodynia) after infusion of prostaglandin $E_2$ ($PGE_2$) into spinal fluid.

The other enzyme is known as hematopoietic prostaglandin D synthase (H-PGDS). This enzyme was first prepared from rat spleen and later identified in the gut and other organs. H-PGDS is a glutathione transferase (sigma type), on the basis of its amino acid sequence and use of glutathione as a cofactor. The enzyme is a homodimer and folds like other glutathione transferases.

When originally discovered, D series prostaglandins were viewed as by-products of prostaglandin E synthesis. However, $PGD_2$ is now known as a regulator of sleep, platelet aggregation, inflammation, smooth muscle contraction, and bronchoconstriction.

BRIEF DESCRIPTION OF THE DRAWINGS

The following illustrations and drawings are by way of example and not by way of limitation. References to "an embodiment" or "one embodiment" in this disclosure are not necessarily to the same embodiment, and such references indicate "at least one embodiment."

FIG. 5A shows the size distribution of small bowel adenomas in 3 H-Pgds$^{-/-}$ mice.

FIG. 5B shows the size distribution of small bowel adenomas in 3 H-Pgds$^{+/-}$ mice.

FIG. 5C shows the size distribution of small bowel adenomas in 3 H-Pgds$^{+/+}$ mice.

FIG. 5D shows the size distribution of colon adenomas in 29 H-Pgds$^{-/-}$ mice.

FIG. 5E shows the size distribution of colon adenomas in 22 H-Pgds$^{+/-}$ mice.

FIG. 5F shows the size distribution of colon adenomas in 22 H-Pgds$^{+/+}$ mice.

DETAILED DESCRIPTION

Figure 1:
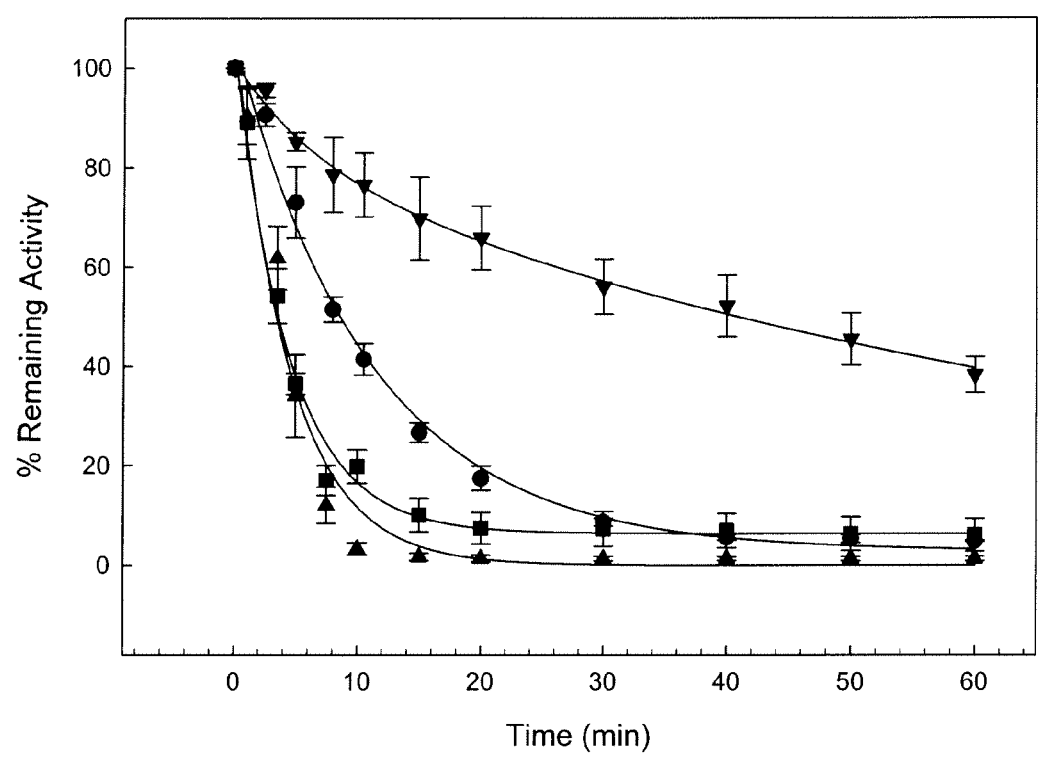
FIG. 1 depicts the thermal stability of the Val187Ile variant of H-PGDS.

Melanoma cells with less PGD2 have been found to cause more metastatic tumors in the lung, when injected into mice [Stringfellow et. al., *Nature* 282, 76-78 (1979)]. PGD$_2$ and derivatives also inhibited growth of leukemic cells in culture and Ehrlich ascites tumors [Fukushima et al., *Biochem. Biophys. Res. Commun.* 109, 626-633 (1982); Kato et al., *Cancer Res.* 46, 3538-3542 (1986); Narumiya et al., *J. Pharmacol. Exp. Ther.* 242, 306-311 (1987)]. Similarly, PGD$_2$ and derivatives (15-deoxy-$\Delta^{12,14}$-PGD$_2$ and 15-deoxy-$\Delta^{12,14}$-PGJ$_2$) reduced growth of prostate cancer cells in tissue culture [Kim et al., *Cancer Res.* 65, 6189-6198 (2005)].

The results documented herein illustrate that high production of PGD$_2$ can prevent tumors, as an additional function. In particular, experiments made use of the Apc$^{Min/+}$ mouse strain, which develops many tumors (adenomas) in the intestines. Loss of H-Pgds in these mice led to 50% more tumors, whereas overproduction of PGD$_2$ due to transgenic H-PGDS or L-PGDS reduced the number of tumors. Thus, the results demonstrate that methods that increase production of PGD$_2$ in the body can inhibit tumor growth and/or development. Similarly, it is believed that treatment agents that increase overall levels or production of PGD$_2$ in the body will inhibit tumor growth.

Therefore, embodiments described here include any method or composition that augments PGD$_2$ production or PGD$_2$ levels in the body and that has cancer chemopreventive properties, suitable for courses of administration, daily use, or other regular use by the population at large or by people with increased risk for cancer. In one embodiment, the method or composition may inhibit tumor growth by increasing PGD$_2$ levels or production within the body. The composition may be an orally or parenterally administered formulation that includes an effective amount of a treatment agent that increases PGD$_2$ levels in the body. The formulation in the effective dosage may be administered on a regular basis, such as once a day.

Representatively, it is contemplated that an effective amount of the treatment agent may be an amount or dosage that augments urinary excretion of PGD$_2$ metabolites by approximately 1.4-1.6-fold or more, when measured over a 24-hour period. This description of an effective amount is based on the observed augmentation of urinary 11β-PGF$_{2\alpha}$ excretion in mice with transgenic H-PGDS. As mentioned above, H-PGDS transgenic mice had a reduced number of intestinal tumors. It is anticipated that the agent will be administered over a prolonged time period, such as years or even decades, when used for cancer chemoprevention. The exact quantities used (e.g., milligrams or grams) will vary depending on pharmacologic properties of the specific agents being used and the routes of administration.

As used herein, suitable agents include, but are not intended to be limited to, drugs, biological treatment agents, chemical treatment agents, therapeutic agents, various enzyme cofactors, bioactive food components, and the like, and pharmaceutical compositions thereof. It is further contemplated that the formulation may include other treatment agents having a cancer chemopreventive effect when administered to the body, such as, for example, tamoxifen or finasteride. Alternatively or additionally, it is contemplated that the formulation may include other agents that may serve to reduce potential undesirable side effects related to increased levels of PGD$_2$, such as, for example, a specific PGD$_2$ receptor antagonist that reduces flushing [Cheng et al. *Proc. Natl. Acad. Sci. USA* 103, 6682-6687 (2006)].

Still further, the formulation may contain compounds or substances that reduce, prevent, or otherwise counteract potential undesirable effects of other prostaglandins ("undesirable prostaglandins"), such as, for instance, PGE$_2$, whose levels may increase within the body as a consequence of certain treatment agents that augment production of PGD$_2$. PGE$_2$ is known to promote tumors. For example, PGE$_2$ and PGD$_2$ both increase in response to nicotinic acid [Benyó et al., *J. Clin. Invest.* 115, 3634-3640 (2005)]. Diferuloylmethane, commonly called curcumin, is a chemical from the turmeric plant that is also believed to have cancer preventive properties. Among other effects, diferuloylmethane reduces transcription of the gene for microsomal prostaglandin E synthase 1 [mPGES-1; Moon et al., *J. Pharmacol. Exp. Ther.* 315, 788-795 (2005)]. Reduced transcription of the mPGES-1 gene would be expected to lower production of PGE$_2$. Additionally, inhibitors of the mPGES-1 enzyme are contemplated, such as a compound designated MK-886 and various γ-hydroxybutenolide derivatives [Riendeau et al., *Bioorg. Med. Chem. Lett.* 15, 3352-3355 (2005); Guerrero et al., *J. Med. Chem.* 50, 2176-2184 (2007)]. Effective mPGES-1 inhibitors would lower PGE$_2$ production within the body.

The formulation and/or treatment agent may be coated with a release delaying layer. In one embodiment, the release delaying layer may be an enteric coating. Typical enteric coatings may include one or more of hydroxypropyl methylcellulose phthalate, hydroxypropyl cellulose acetyl succinate, cellulose acetate phthalate, polyvinyl acetate phthalate, or methacrylic acid-methyl methacrylate copolymers. For example, the formulation may be in the form of a tablet entirely covered with the enteric coating, or individual particles of the treatment agent may be coated with the release delaying layer and then compressed into a tablet. Absorption of the treatment agent may primarily occur in the intestine, and in particular, the colon instead of the liver, thereby avoiding metabolism by the liver and reducing potential liver toxicity.

Still further, the formulation may include additional release delaying coatings having a property to further control a release rate of the treatment agent incorporated therein. In one embodiment, the coating may provide for extended release of the treatment agent, such as, for example, a coating including a hydroxypropyl methylcellulose and/or a hydrophobic component. In this aspect, significant quantities of the treatment agent may be released for absorption into the blood stream over specific timed intervals, in this case over an extended period, such as 12 hours or longer, e.g. 12-24 hours, after ingestion. For some drug formulations, extended release (ER) components can also be referred to as sustained release (SR) or prolonged release (PR). Alternatively, the coating may be a type that allows for immediate release of the treatment agent. In this aspect, the treatment agent may be released substantially immediately upon contact with gastric juices and will result in substantially complete dissolution within, for example, about 1 hour. Immediate release (IR) components can also be referred to as instant release. It is contemplated that the immediate release coating may be any conventional coating suitable for allowing for release of the treatment agent within about 1 to 2 hours. It is further contemplated that any type of release controlling coating and technique conventionally known may be utilized as deemed desirable for controlling a release rate of the treatment agent.

As discussed above, in one embodiment, the formulation may be compressed into a pellet and covered with the enteric coating. In this aspect, the formulation may be a mixture of excipients to fulfill the function of, for example, a filler, a binder, a disintegrant, and a lubricant along with an effective amount of the treatment agent. Optionally, the formulation may also contain other ingredients such as flavors and colors. A wet granulation technique may be used to provide a core formulation that may be extruded to form pellets according to any technique deemed desirable. Once dried, the pellets may be coated with the enteric coating by use of any technique deemed desirable, for example, a fluidized process. In embodiments for which a further release-delaying coating are provided, for example an extended release coating, the extended release coating may be applied to the treatment agent prior to forming the tablet or alternatively, to the pellet prior to coating the pellet with the enteric coating.

In still further embodiments, a formulation including one of, or a combination of, the above-described treatment agents may be introduced into the body in any manner found suitable for administering an effective amount of the treatment agent to inhibit tumor growth. For example, it is contemplated that the treatment agent may be in the form of an oral liquid or may be administered topically, transdermally, or transcutaneously, for example, via an adhesive patch applied to the skin.

Alternatively or additionally, the treatment agent may be a prostaglandin D synthase enzyme or a product or metabolite thereof. Representative products or metabolites may include, but are not limited to, $PGD_2$ or 15-deoxy-$\Delta^{12,14}$-$PGJ_2$. Representative prostaglandin D synthase enzymes may include, but are not limited to, H-PGDS, L-PGDS, or related enzymes that remain to be identified. A sequence listing for H-PGDS is included and referred to herein as SEQ ID NO 1. The H-PGDS structure designated by SEQ ID NO 1 corresponds to the following accession numbers in databases of the National Center for Biotechnology Information (NCBI): Protein ID NP_055300.1, prostaglandin-D synthase [*Homo sapiens*]; Nucleotide ID NM_014485.2, *Homo sapiens* prostaglandin $D_2$ synthase, hematopoietic (PGDS), mRNA; CCDS ID 3640.1, *Homo sapiens* PGDS; and GeneID 27306, PGDS prostaglandin D2 synthase, hematopoietic [*Homo sapiens*]. When embodiments contain prostaglandin D synthase enzymes, it is contemplated that the treatment agents may need to be administered by parenteral routes, such as infusion into a vein.

Further, when treatment agents contain a prostaglandin D synthase, the enzyme used may be a variant form that has been designed, produced, modified, or "engineered" by recombinant DNA technology, site-directed mutagenesis, or other molecular genetic methods. Engineered enzymes may have desirable properties that are not found in the wild-type enzyme, such as greater activity, higher stability, or propensity or tendency to enter certain cells where production of $PGD_2$ may be especially beneficial.

An example of an engineered H-PGDS enzyme that exhibits high stability is based on a naturally occurring variant, in which the amino acid valine at position 187 is replaced by isoleucine (designated the Val187Ile variant). As detailed in Example III, the Val187Ile variant was identified by screening H-PGDS genes from 94 blood specimens (47 African American and 47 white) by use of a method known as DNA heteroduplex analysis. The exact gene mutation was then established by DNA sequencing. Two other variant H-PGDS enzymes were also detected by these methods (Ile91Val and Met128Thr). The wild-type and three variant enzymes were produced in bacteria and purified for measurement of enzyme activity and stability. Specific activities (glutathione transferase activities) were found to be similar for the four enzymes.

Table 1 and FIG. 1 show the high thermal stability of the Val187Ile variant, in comparison to the wild-type enzyme and the two other variants (Ile91Val and Met128Thr). Each enzyme was incubated at 50° C. for the indicated times, followed by immediate assay of glutathione transferase activity with 1-chloro-2,4-dinitrobenzene as the substrate (see Example II for details). Symbols in FIG. 1 are: ●, H-PGDS wild-type; ■, Ile91Val variant; ▲, Met128Thr variant; ▼, Val187Ile variant. The initial activity was set to 100% activity for each assay. Data were averaged from three independent assays and were fit to curves for exponential decline. The half-life at 50° C. for the Val187Ile variant was roughly 42 minutes, compared to 9 minutes or less for the wild-type and the other variants. The difference was statistically significant ($P<0.05$; analysis of variance with Dunnett's method). It should be noted that the Val187Ile variant also has high stability at physiological temperatures (37° C.).

TABLE 1

Specific activities and thermal stabilities of H-PGDS enzymes prepared by bacterial expression

| H-PGDS enzyme | Specific activity [μmol of product/min/ mg of protein] | Half-life at 50° C. [min] |
|---|---|---|
| Wild-type | 5.8 ± 0.2 | 8.6 ± 0.1 |
| Ile91Val variant | 4.2 ± 0.1 | 4.3 ± 1.9 |
| Met128Thr variant | 3.0 ± 0.1 | 2.0 ± 0.5 |
| Val187Ile variant | 4.7 ± 0.5 | 41.7 ± 9.3 |

As used herein, the term "Val187Ile variant" includes or refers to any deoxyribonucleic acid sequence of the H-PGDS gene, any ribonucleic acid sequence of H-PGDS transcription products, or any amino acid sequence of the H-PGDS enzyme or protein that is characterized by, or results in, substitution of amino acid valine by isoleucine at position 187 of the hematopoietic prostaglandin D synthase enzyme. Thus, embodiments herein referred to as the Val187Ile variant also include gene sequences, DNA clones, gene expression vectors, viral vectors, or similar DNA structures or constructions related to production of the Val187Ile form of H-PGDS in the human body, living cells (such as, but not limited to, tissue culture cells), or organisms of any kind (prokaryotic or eukaryotic).

Figure 2A:
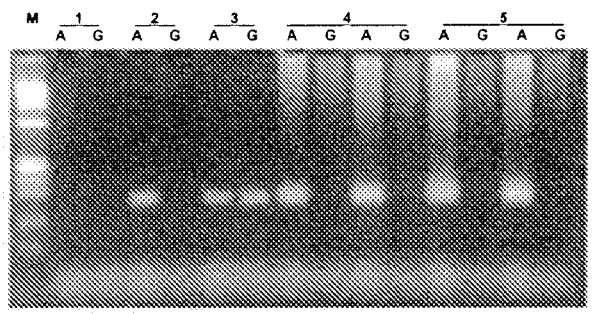
FIG. 2A shows detection of the Ile91Val variant (c.271 A>G) by use of allele-specific PCR.
Figure 2B:
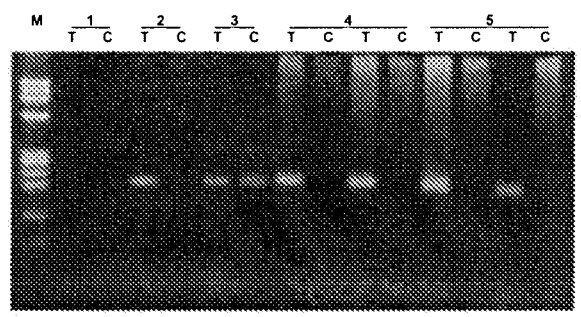
FIG. 2B shows detection of the Met128Thr variant (c.383 T>C) by use of allele-specific PCR.
Figure 2C:
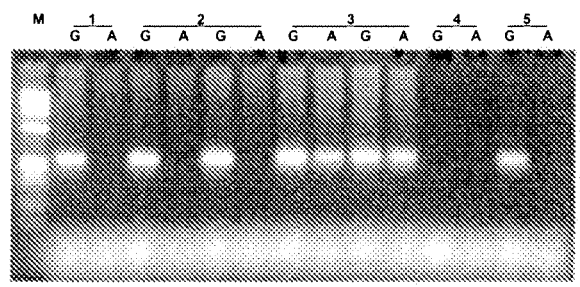
FIG. 2C shows detection of the Val187Ile variant (c.559 C>G) by use of allele-specific PCR.

Val187Ile gene sequences in an individual may be molecularly identified by a variety of methods, including DNA sequencing and allele-specific PCR. FIGS. 2A-2C illustrate detection and confirmation of human H-PGDS variants, by use of allele-specific PCR. Example II describes the materials and conditions used. "M" indicates DNA size markers (φX174 RF HaeIII digest). FIG. 2A shows detection of the Ile91Val variant (c.271 A>G). "A" indicates PCR with the wild-type primer, and "G" indicates PCR with the variant primer. Specimen 1 is a negative control (no DNA). Specimen 2 is a wild-type control. Specimen 3 is a variant control (heterozygote). Specimens 4 and 5 are heterozygous variants (each specimen tested in duplicate). FIG. 2B shows detection of the Met128Thr variant (c.383 T>C). "T" indicates PCR with the wild-type primer, and "C" indicates PCR with the variant primer. Specimen 1 is a negative control (no DNA). Specimen 2 is a wild-type control. Specimen 3 is a variant control (heterozygote). Specimens 4 and 5 are heterozygous variants (each specimen tested in duplicate). FIG. 2C shows detection of the Val187Ile variant (c.559 C>G). "C" indicates PCR with the wild-type primer, and "G" indicates PCR with the variant primer. Specimen 1 is homozygous wild-type. Specimen 2 is homozygous wild-type (tested in duplicate).

Specimen 3 is a heterozygous variant (tested in duplicate). Specimen 4 is a negative control (no DNA). Specimen 5 is a wild-type control.

Thus, other possible uses of the Val187Ile variant (as defined above) include identification, for any purpose, of individuals who carry the Val187Ile gene variant (or allele). Such purposes may include assessing: predisposition to increased risk for a disease; predisposition to reduced risk for a disease; predisposition to adverse effects of drugs, other pharmacologic agents, vitamins, nutritional supplements, or foods; predisposition to beneficial effects of drugs, other pharmacologic agents, vitamins, nutritional supplements, or foods; or predisposition to augmented $PGD_2$ production in the body.

Example III as described herein shows the details of the discovery, identification, construction, and properties of the Val187Ile form of H-PGDS. As discussed above, this variant is far more stable than the most common form of the H-PGDS enzyme. The Val187Ile form of H-PGDS therefore represents a further embodiment for increasing $PGD_2$ production above levels usually found in the body.

As an introduction to the sections below describing tumor suppression, it is believed that the embodiments described will have a cancer chemopreventive effect when administered to mammals, and in particular humans. Chemoprevention in this sense relates to the use of a treatment agent to reduce the risk for cancer, or to delay its development or recurrence. It is known that PGE2 promotes colon neoplasia, on the basis of knockout mouse studies on enzymes and receptors in the prostaglandin cascade. On the other hand, earlier reports suggested that PGD2 may suppress tumors. However, a role in tumor development has not been previously recognized for enzymes specifically involved in biosynthesis of PGD2 in the body. These enzymes include H-PGDS and L-PGDS.

Examples I and II as described herein made use of the Apc$^{Min/+}$ mouse strain. The strain was originally produced by ethylnitrosourea, which caused a nonsense mutation at codon 850 (out of 2845) in the adenomatous polyposis coli gene (Apc) [Su et al., Science 256, 668-670 (1992)]. Heterozygous mice (Apc$^{Min/+}$) develop many adenomas in the intestines, from the duodenum to the colon (multiple intestinal neoplasia, or Min), resembling familial adenomatous polyposis in humans. The Apc$^{Min/+}$ mouse strain is widely recognized as a tool for experimental research on intestinal cancer. Thus, in Examples I and II, Apc$^{Min/+}$ mice were bred with H-Pgds knockout, L-Pgds knockout, H-PGDS transgenic, or L-PGDS transgenic mice in order to assess the influence of manipulating $PGD_2$ production on development of intestinal adenomas.

The description that follows shows that homozygous or heterozygous disruption of the gene for H-Pgds in Apc$^{Min/+}$ mice led to roughly 50% more intestinal adenomas, compared to controls. H-Pgds was detected by immunohistochemistry, mainly in macrophages and monocytes of the gut mucosa. The numbers of tumors did not increase following knockout of the gene for L-Pgds, which is not produced in the intestine. Additionally, Apc$^{Min/+}$ mice with transgenic human H-PGDS or L-PGDS produced in all cell types had 35-70% fewer intestinal adenomas.

The results described thus support an interpretation that prostaglandin D synthase enzymes control an inhibitory effect on intestinal tumors. It is therefore believed that raising levels of PGD2 or its metabolites or augmenting PGD2 production in the intestines (or other organs in the body) through manipulating $PGD_2$ biosynthetic enzymes may be useful for prevention of cancer, particularly intestinal cancer.

Several enzymes are known to take part in $PGD_2$ biosynthesis in the body. These individual enzymes are essential parts of biochemical pathways responsible for $PGD_2$ production in the body and include: cytosolic phospholipase $A_2$ (also known as cPLA$_2$), cyclooxygenase-1 (also known as Cox-1 or PTGS1), cyclooxygenase-2 (also known as Cox-2 or PTGS2), H-PGDS, and L-PGDS. It is also known that $PGD_2$ can convert without enzymes to additional metabolites that potentially take part in tumor suppression, such as (but not restricted to) 15-deoxy-$\Delta^{12,14}$-PGJ$_2$.

Manipulation or augmentation of $PGD_2$ production in the body is illustrated by effects of niacin (the nicotinic acid form of vitamin B3). Oral niacin is used to treat lipid disorders at doses of up to three grams per day. Upon distribution to tissues, niacin binds to the G-protein coupled receptor, GPR109A, whose gene is expressed in the skin and other organs, including the intestines. Niacin binding to GPR109A is believed to cause internalization of the receptor, calcium mobilization, and phosphorylation and activation of cPLA$_2$, the first enzyme in the prostaglandin biosynthetic pathway [Tang et al., Biochem. Biophys. Res. Commun. 345, 29-37 (2006); Richman et al., J. Biol. Chem. 282, 18028-18036 (2007)]. The result is a marked rise in $PGD_2$ production in the skin (causing flushing, or dilatation of the arterioles in the skin and a burning or warm sensation), as well as higher levels of $PGE_2$ and $PGI_2$ (or, prostacyclin). Thus, niacin augments $PGD_2$ production by stimulating biosynthesis of prostaglandins in general.

The concept of augmenting $PGD_2$ production by stimulating an enzyme involved in its biosynthesis is further illustrated by a factor known as Ras guanine nucleotide-releasing protein 4 (designated RasGRP4). This protein molecule stimulates transcription of the H-PGDS gene in a human mast cell line known as HMC-1. Specifically, HMC-1 cells that contained RasGRP4 had 100-fold higher transcription of the H-PGDS gene and 12-20-fold more $PGD_2$, compared to HMC-1 cells that lacked RasGRP4 [Li et al., J. Biol. Chem. 278, 4725-4729 (2003)]. Thus, activation of the H-PGDS gene by RasGRP4 in specific cells augmented $PGD_2$ production in those cells.

Thus, the disclosure describes raising $PGD_2$ production in the body to inhibit intestinal tumors. Data from Example I has been described in Park et al. [Cancer Res. 67, 881-889, 2007]. Although inhibition of intestinal tumors is documented in this disclosure, it is further contemplated that raising PGD2 production in the body will result in inhibition of other types of non-cutaneous tumors.

Mouse and human H-PGDS genes have 6 exons, encoding 199 amino acids. A mouse strain deficient in H-Pgds, such as by virtue of knockout of a portion of the H-Pgds gene, was available before the work described herein. Homozygous H-Pgds knockout mice (H-Pgds$^{-/-}$) produce no H-Pgds enzyme. Similarly, a mouse strain deficient in L-Pgds was also available. Both strains were provided by the Osaka Bioscience Institute [Osaka, Japan].

As part of the work described, intercrosses of heterozygous H-Pgds knockout mice (H-Pgds$^{+/-}$×H-Pgds$^{+/-}$, including some with Apc$^{Min/+}$) yielded offspring in expected 1:2:1 ratios: 27.8% H-Pgds$^{-/-}$ (22 of 79 mice); 45.6% H-Pgds$^{+/-}$ (36 of 79); and 26.6% H-Pgds$^{+/+}$ (21 of 79; $\chi^2$=0.65; P=0.72). Thus, there was no sign of embryonic lethality. H-Pgds$^{-/-}$ mice developed normally. Average weights at 10 weeks indicated no difference in growth between H-Pgds$^{-/-}$ (21.7 g for 6 mice) and wild-type mice.

Mouse strains that overproduce either human H-PGDS or L-PGDS (by virtue of carrying a human H-PGDS or L-PGDS coding sequence, i.e., H-PGDS or L-PGDS transgenic mice, respectively) were available from the Osaka Bioscience Institute [Osaka, Japan]. Construction of the introduced gene was described by Pinzar et al. [J. Biol. Chem. 275, 31239-31244, (2000)]. H-PGDS and L-PGDS transgenic mice used for the work described were of a mixed background (C57BL/6× FVB/N). Such mice appeared healthy, had normal growth, and produced offspring.

Further, the H-PGDS transgenic mice had high production of human H-PGDS mRNA in colon tissue, as shown by reverse transcription and quantitative polymerase chain reaction assays. Specifically, wild-type (non-transgenic) mice had 998 to 6,090 copies of mouse H-Pgds mRNA transcripts per ng of total RNA. The geometric mean was $2.0 \times 10^3$ copies, on the basis of measurements on four mice. In contrast, H-PGDS transgenic mice had 5.97 and $9.45 \times 10^5$ copies of human H-PGDS mRNA transcripts per ng of total RNA. The geometric mean was $7.5 \times 10^5$ copies, on the basis of measurements on two transgenic mice. The mean copy numbers from these determinations indicate a 375-fold increase in expression of transgenic H-PGDS over endogenous mouse H-Pgds. Expression of transgenic L-PGDS was expected to be comparable to expression of transgenic H-PGDS, because the gene control elements joined to the H-PGDS and L-PGDS genes in the expression vectors were the same (i.e., the cytomegalovirus immediate early enhancer, the chicken β-actin promoter, and the rabbit β-globin polyadenylation signal).

Figure 3A:
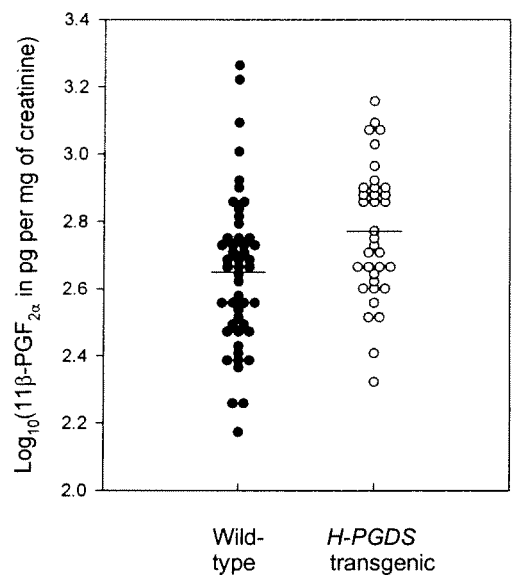
FIG. 3A shows urine 11β-$PGF_{2α}$ (a metabolite of $PGD_2$) in wild-type and H-PGDS transgenic mice.

$PGD_2$ degrades rapidly in the body and is removed from circulating blood. $11\beta$-$PGF_{2\alpha}$ is the first metabolite that appears in the urine and is an indicator of the amount of $PGD_2$ made in the body [O'Sullivan et al., *Prostaglandins Other Lipid Mediat.* 57, 149-165 (1999)]. FIG. 3A shows urine $11\beta$-$PGF_{2\alpha}$ in wild-type and H-PGDS transgenic mice. The graph represents 84 urine collections from 37 mice (1-9 urine collections per mouse). Three of the points each show the result of a single measurement, whereas all other points represent the average of at least two measurements at different dilutions of urine. Excretion of $11\beta$-$PGF_{2\alpha}$ varied from 140 to 1,700 pg per mg of creatinine for mice with wild-type H-Pgds genes (geometric mean, 460). H-PGDS transgenic mice tended to have more $11\beta$-$PGF_{2\alpha}$ in the urine (geometric mean, 630; 1.4-fold higher; 95% confidence interval, 0.94-2.0). However, the difference observed between wild-type and transgenic mice was not statistically significant (one-way mixed model analysis of variance for these two groups; two-tailed; P=0.09). Horizontal bars indicate means of the points, which are slightly different from geometric means found by mixed model analysis of variance.

Figure 3B:
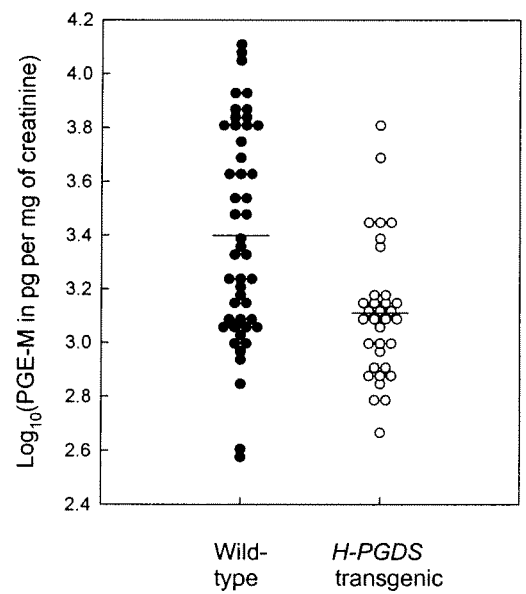
FIG. 3B shows urine PGE-M (prostaglandin E metabolite) in wild-type and H-PGDS transgenic mice.

Similarly, $PGE_2$ is rapidly catabolized in the lungs, and urinary PGE-M reflects the amount of $PGE_2$ produced in tissues [Gross et al., *Clin. Cancer Res.* 11, 6087-6093 (2005)]. PGE-M is also known as prostaglandin E metabolite, or 9,15-dioxo-11α-hydroxy-2,3,4,5-tetranor-prostan-1,20-dioic acid. FIG. 3B shows urine PGE-M in wild-type and H-PGDS transgenic mice. The graph represents 82 urine collections from 34 mice. Two of the points each show the result of a single measurement, whereas all other points represent the average of at least two determinations at different urine dilutions. Urinary excretion of PGE-M varied from 390 to 12,400 pg per mg of creatinine for wild-type mice (geometric mean, 2,520). H-PGDS transgenic mice tended to have less PGE-M in the urine (geometric mean, 1,613; 0.64-fold lower; 95% confidence interval, 0.32-1.26). However, the difference seen between wild-type and transgenic mice was not statistically significant (one-way mixed model analysis of variance for these two groups; two-tailed; P=0.19). Horizontal bars indicate means of the points shown.

Adenomas in both the small bowel and the colon of $Apc^{Min/+}$ mice with H-Pgds or L-Pgds gene knockouts were counted histologically by sacrificing the mice at 14 weeks. The entire intestine was prepared like a Swiss roll, embedded in paraffin, and cut into sections for mounting on slides for microscopic analysis. In the description herein, tumors were identified and counted in 18 sections spaced 250 micrometers (μm) apart. By this method, nearly the entire intestine was inspected, except regions in partial sections at the beginning and end of each paraffin block.

Similarly, adenomas in both the small bowel and the colon of $Apc^{Min/+}$ mice with transgenic human H-PGDS or L-PGDS were counted by sacrificing the mice at 14 weeks of age and preparing slides as described above, except 24 sections spaced 150 μm apart were examined. More sections were used for transgenic mice than for knockout mice, in case the transgenic mice had substantially fewer adenomas, due to the transgene or to the hybrid genetic background of the mice (C57BL/6×FVB/N, versus C57BL/6 for H-Pgds knockout mice). For example, $Apc^{Min/+}$ mice on a hybrid C57BL/6× AKR background may have roughly 80% fewer tumors than C57BL/6 $Apc^{Min/+}$ mice. Use of sections spaced 150 μm apart should allow detection of a higher proportion of small adenomas in the sectioned region. Therefore, data for H-PGDS and L-PGDS transgenic mice versus data for H-Pgds knockout mice are not directly comparable.

As seen from Table 2, more than 95% of the adenomas in $Apc^{Min/+}$ mice occurred in the small bowel. $Apc^{Min/+}$ mice that were homozygous or heterozygous for the H-Pgds knockout had 44-61% more intestinal adenomas than did $Apc^{Min/+}$ mice with wild-type H-Pgds. Colon adenomas increased two-fold in H-Pgds knockout mice. There was no statistical difference between numbers of adenomas in H-Pgds$^{-/-}$ versus H-Pgds$^{+/-}$ mice. Numbers of adenomas in $Apc^{Min/+}$ mice homozygous for L-Pgds knockouts were not different from controls. In contrast, $Apc^{Min/+}$ mice with H-PGDS transgenes had 70% fewer adenomas than controls, in both the small bowel and the colon.

TABLE 2

Adenomas in $Apc^{Min/+}$ mice with hematopoietic prostaglandin D synthase knockouts or transgenes A. Numbers of adenomas in the entire intestine

|  | Knockout mice | | | Controls |
| --- | --- | --- | --- | --- |
|  | H-Pgds$^{-/-}$ | H-Pgds$^{+/-}$ | L-Pgds$^{-/-}$ | $Apc^{Min/+}$ |
| Geometric mean | 224 | 250 | 146 | 155 |
| Range | 113-652 | 128-614 | 85-273 | 57-247 |
| No. of mice | 29 | 22 | 12 | 22 |
| P-value | <0.001 | <0.0001 | NS | — |

|  | Transgenic mice H-PGDS$^{TG}$ | Controls $Apc^{Min/+}$ |
| --- | --- | --- |
| Geometric mean | 33 | 119 |
| Range | 6-251 | 47-436 |
| No. of mice | 24 | 15 |
| P-value | <0.0001 | — |

B. Numbers of adenomas in the colon

|  | Knockout mice | | | Controls |
| --- | --- | --- | --- | --- |
|  | H-Pgds$^{-/-}$ | H-Pgds$^{+/-}$ | L-Pgds$^{-/-}$ | $Apc^{Min/+}$ |
| Geometric mean | 8.2 | 8.2 | 3.6 | 4.0 |
| Range | 2-21 | 1-22 | 1-9 | 1-12 |

TABLE 2-continued

Adenomas in Apc$^{Min/+}$ mice with hematopoietic
prostaglandin D synthase knockouts or transgenes

| No. of mice | 29 | 22 | 12 | 22 |
|---|---|---|---|---|
| P-value | <0.01 | <0.01 | NS | — |

| | Transgenic mice H-PGDS$^{TG}$ | Controls Apc$^{Min/+}$ |
|---|---|---|
| Geometric mean | 2.2 | 7.4 |
| Range | 0-7 | 1-26 |
| No. of mice | 24 | 15 |
| P-value | <0.001 | — |

C. Sizes of adenomas in the small bowel

| | H-Pgds$^{-/-}$ | H-Pgds$^{+/-}$ | Apc$^{Min/+}$ |
|---|---|---|---|
| No. of mice analyzed | 3 | 3 | 3 |
| No. of adenomas measured | 653 | 653 | 470 |
| Size range, mm | 0.1-2.1 | 0.1-2.2 | 0.1-2.5 |
| Median size, mm | 0.38 | 0.38 | 0.62 |
| Average size, mm | 0.51 | 0.49 | 0.68 |

D. Sizes of adenomas in the colon

| | H-Pgds$^{-/-}$ | H-Pgds$^{+/-}$ | Apc$^{Min/+}$ |
|---|---|---|---|
| No. of mice analyzed | 29 | 22 | 22 |
| No. of adenomas measured | 271 | 223 | 102 |
| Size range, mm | 0.1-4.1 | 0.1-4.3 | 0.1-4.6 |
| Median size, mm | 0.12 | 0.20 | 0.12 |
| Average size, mm | 0.57 | 0.94 | 0.72 |

P-values for the knockout mice refer to a comparison between the indicated genotype and controls (Apc$^{Min/+}$), by use of nonparametric tests (Mann-Whitney with Bonferroni corrections). NS indicates not statistically significant. The P-values for transgenic mice refer to comparison between H-PGDS transgenic mice and controls (Apc$^{Min/+}$), by the t-test. Numbers of adenomas were converted to their logarithms (base 10), before performing statistical tests.
A value of 0.5 was added to the numbers of colon adenomas in transgenic mice and controls before transforming data to logarithms (for statistical calculations), because three transgenic mice had zero colon adenomas. However, the ranges shown are the observed values.
For measurement of adenomas in the small bowel, three mice for each of the three genotypes were used. The numbers of adenomas for each of these mice were close to the median number of adenomas for all mice with the same genotype.

Figure 4A:
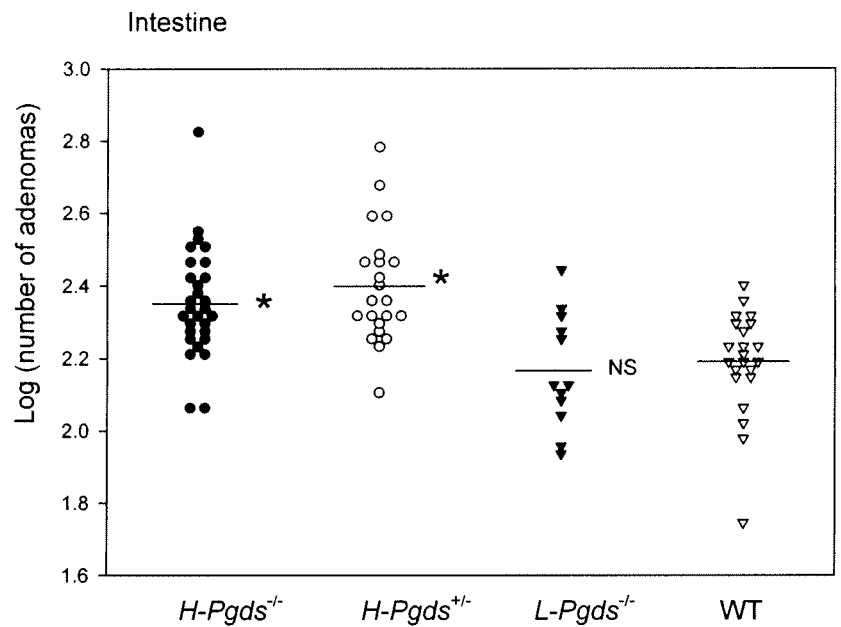
FIG. 4A represents adenomas in the entire intestine of Pgds knockout mice and controls.
Figure 4B:
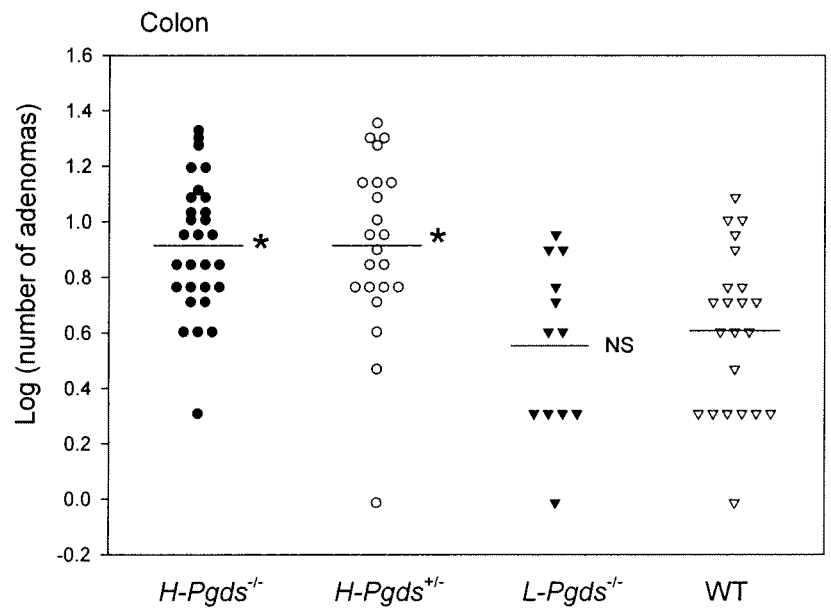
FIG. 4B represents colon adenomas in Pgds knockout mice and controls.
Figure 4C:
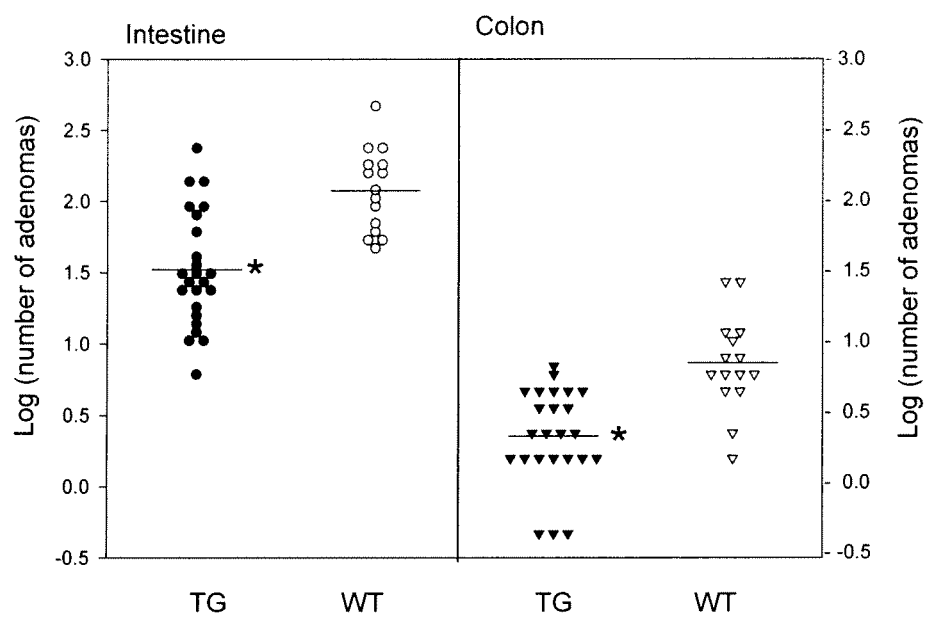
FIG. 4C represents adenomas in the entire intestine and in the colon of H-PGDS transgenic mice and controls.

Numbers of adenomas in the intestines of H-Pgds knockout mice, H-PGDS transgenic mice, and controls are illustrated in FIGS. 4A-4C. FIG. 4A shows the number of adenomas in the entire intestine of Pgds knockout mice and controls. H-Pgds$^{-/-}$ indicates homozygous H-Pgds knockout mice. H-Pgds$^{+/-}$ indicates heterozygous H-Pgds knockout mice, and L-Pgds$^{-/-}$ indicates homozygous lipocalin-type Pgds knockout mice. WT indicates control mice (Apc$^{Min/+}$). Plotted points represent logarithms of the numbers of adenomas. Horizontal bars show means. An asterisk (*) indicates a statistically significant difference (P<0.05) between the indicated genotype and controls, whereas "NS" indicates a non-significant difference. FIG. 4B shows colon adenomas in Pgds knockout mice and controls. Labeling is the same as in FIG. 4A. FIG. 4C shows adenomas in the entire intestine (left panel) and in the colon (right panel) of H-PGDS transgenic mice and controls. TG indicates H-PGDS transgenic mice, and WT represents control mice (Apc$^{Min/+}$). A value of 0.5 was added to all numbers of colon adenomas before taking the logarithm, because three transgenic mice had zero colon adenomas.

The distribution of sizes of adenomas was fairly similar among H-Pgds knockout mice, H-PGDS transgenic mice, and controls. FIGS. 5A-5F represent sizes of adenomas in the small bowel and colon from H-Pgds knockout mice and controls. FIGS. 5A-5C show sizes of 1,776 adenomas in the small bowel in nine Apc$^{Min/+}$ mice (three mice each with H-Pgds$^{-/-}$, H-Pgds$^{+/-}$, H-Pgds$^{+/+}$ genotypes). FIG. 5A shows a size distribution of small bowel adenomas in three H-Pgds$^{-/-}$ mice. FIG. 5B shows a size distribution of small bowel adenomas in three H-Pgds$^{+/-}$ mice. FIG. 5C shows a size distribution of small bowel adenomas in three H-Pgds$^{+/+}$ mice. Mice were used whose numbers of adenomas were very close to the median number for their genotype. Sizes ranged from 0.1 to 2.5 mm, as measured under the microscope. The smallest adenomas were microscopic foci of dysplastic cells. Adenomas in mice with H-Pgds knockouts tended to be smaller than adenomas in controls. For example, average sizes for H-Pgds$^{+/-}$ and H-Pgds$^{-/-}$ mice were 0.49-0.51 mm, compared to 0.68 mm for H-Pgds$^{+/+}$ mice. However, differences were not assessed statistically. FIGS. 5D-5F show sizes of 596 colon adenomas in a total of 73 mice. Mice with L-Pgds knockouts were excluded from the description. FIG. 5D shows a size distribution of colon adenomas in 29 H-Pgds$^{-/-}$ mice. FIG. 5E shows a size distribution of colon adenomas in 22 H-Pgds$^{+/-}$ mice. FIG. 5F shows a size distribution of colon adenomas in 22 H-Pgds$^{+/+}$ mice. Adenoma sizes ranged from 0.1 to 4.6 mm, although most were smaller than 1 mm. Judging from the variation seen, there appeared to be no difference in sizes of colon adenomas across H-Pgds genotypes. Sizes of adenomas in H-PGDS transgenic mice also appeared similar to sizes for controls (not shown).

Immunohistochemistry was used to detect H-Pgds in the intestinal mucosa. Intestines from mice with homozygous H-Pgds gene knockouts did not stain with anti-H-Pgds antibodies, under these conditions. H-Pgds was detected in macrophages and monocytes in the intestinal mucosa of wild-type mice. Mast cells also may stain for H-Pgds, but there were only a few mast cells in the tissues analyzed. Peyer's patches showed scattered H-Pgds-positive cells rather than uniform staining, supporting an interpretation that stained cells are not lymphocytes. No H-Pgds was detected in fibroblasts, endothelial cells, or epithelium, as judged by cell morphology or location. The avidin-biotin-peroxidase reactions in these staining procedures were performed in 0.35 M NaCl, in order to prevent nonspecific staining of mast cells [Jones et al., Histochem. J. 19, 264-268 (1987)].

Figure 6A:
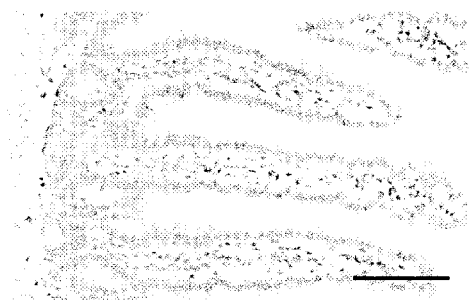
FIG. 6A represents immunoperoxidase staining of mouse intestines with anti-mouse H-Pgds antibodies and shows a section through villi from an H-Pgds$^{-/-}$ mouse, with no antibody staining detectable.
Figure 6D:
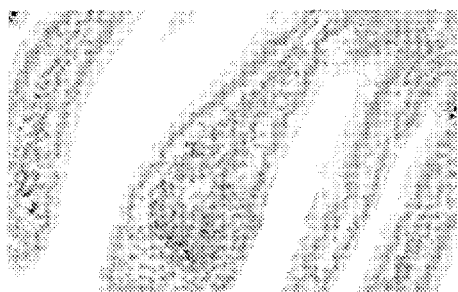
FIG. 6D represents immunoperoxidase staining of mouse intestines with anti-mouse H-Pgds antibodies and represents sections through villi from H-Pgds$^{+/+}$ mice, showing staining in the mucosal stroma.
Figure 6B:
FIG. 6B represents immunoperoxidase staining of mouse intestines with anti-mouse H-Pgds antibodies and shows a section through a Peyer's patch from an H-Pgds$^{-/-}$ mouse, with no apparent antibody staining.
Figure 6E:
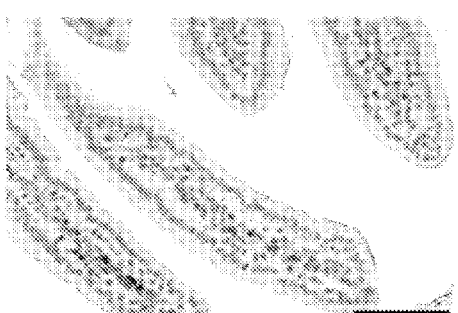
FIG. 6E represents immunoperoxidase staining of mouse intestines with anti-mouse H-Pgds antibodies and represents sections through villi from H-Pgds$^{+/+}$ mice, showing staining in the mucosal stroma.
Figure 6C:
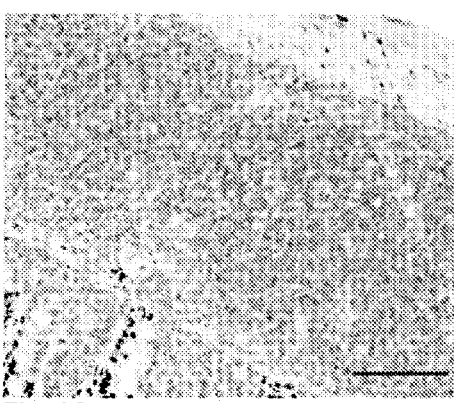
FIG. 6C represents immunoperoxidase staining of mouse intestines with anti-mouse H-Pgds antibodies and represents a section through a Peyer's patch from an H-Pgds$^{+/+}$ mouse, showing antibody staining.
Figure 6F:
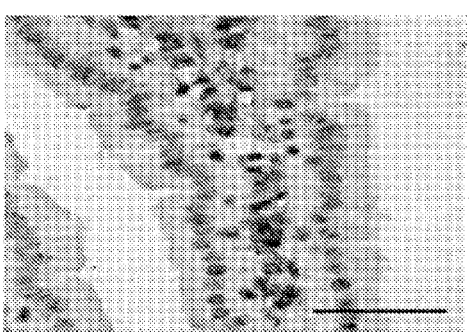
FIG. 6F represents immunoperoxidase staining of mouse intestines with anti-mouse H-Pgds antibodies and shows a section through villi from H-Pgds$^{+/+}$ mice, as in FIGS. 6D-6E but at a higher magnification.

FIGS. 6A-6F illustrate the immunoperoxidase staining of mouse intestines with anti-mouse H-Pgds antibodies. A scale bar of 50 μm is shown. Intestines from mice with homozygous H-Pgds gene knockouts did not stain with anti-H-Pgds antibodies, as mentioned above. FIG. 6A represents a section through villi from an H-Pgds$^{-/-}$ mouse, with no antibody staining detectable. FIG. 6B represents a section through a Peyer's patch from an H-Pgds$^{-/-}$ mouse, with no apparent antibody staining. FIG. 6C represents a section through a Peyer's patch from an H-Pgds$^{+/+}$ mouse, showing antibody staining. H-Pgds staining was clearly indicated by brown staining on the original histologic sections, but appears as dark granules or spots in the half-tone prints. FIGS. 6D-6E represent sections through villi from H-Pgds$^{+/+}$ mice, showing staining in the mucosal stroma. FIG. 6F represents a section through villi from H-Pgds$^{+/+}$ mice as in FIGS. 6D-6E, but at a higher magnification.

Figure 7A:
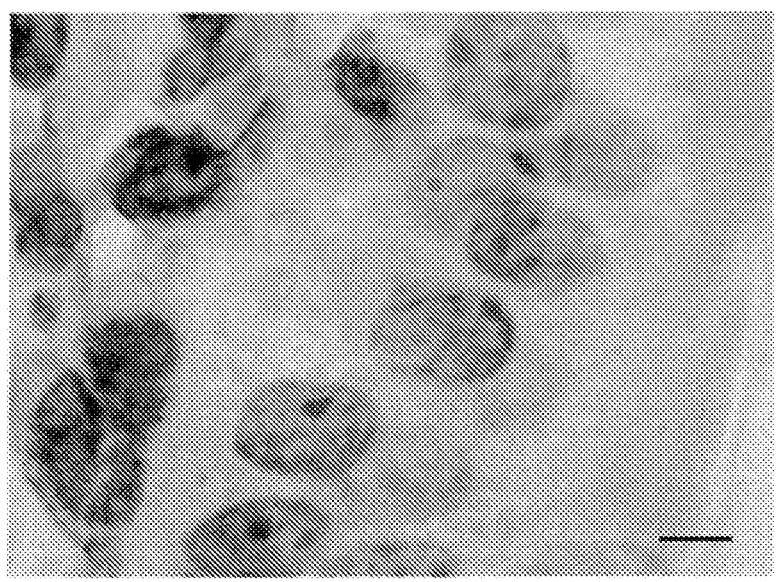
FIG. 7A represents staining of H-Pgds in macrophages and monocytes of the mouse intestine, but generally not in other stromal cells or in the epithelium.
Figure 7B:
FIG. 7B represents staining of H-Pgds in macrophages and monocytes of the mouse intestine, but generally not in other stromal cells or in the epithelium.

Further, FIGS. 7A-7B represent staining of H-Pgds in macrophages and monocytes of the mouse intestine, but generally not in other stromal cells or in the epithelium. A scale bar of 5 μm is shown. H-Pgds is clearly indicated by brown staining on the original histologic sections, but as dark shading surrounding cell nuclei in the prints shown. FIGS. 7A-7B show peroxidase-stained, H-Pgds-positive cells, which were rounded or oval in shape. Nuclei were kidney-shaped with small nucleoli, characteristic of macrophages.

Thus, to summarize results shown in Table 2 and FIGS. 4A-7B, roughly 50% more small bowel adenomas and a two-fold increase in colon adenomas occurred in Apc$^{Min/+}$ mice deficient in H-Pgds (either homozygous or heterozygous knockouts). Homozygous knockout of L-Pgds did not affect intestinal adenomas, most likely because the "brain" type of the enzyme is nearly absent in the gut. Conversely, 70% fewer adenomas were found in Apc$^{Min/+}$ mice with transgenic H-PGDS. The drop occurred in both the small bowel and colon. Fewer adenomas in H-PGDS transgenic mice and more adenomas in H-Pgds knockout mice strongly support the conclusion that H-PGDS, PGD$_2$, or metabolites can inhibit tumors.

As previously discussed, potential mechanisms for tumor suppression may include action of PGD$_2$ or its metabolites. For example, PGD2 converts without enzymes to 15-deoxy-$\Delta^{12,14}$-PGJ$_2$. The compound is a naturally occurring ligand for PPARγ, and binding induces enzymatic conjugation of SUMO-1 (small ubiquitin-related modifier-1) to lysine 365 in the PPARγ ligand binding domain. SUMOylation, in turn, is thought to increase PPARγ binding to nuclear receptor corepressor complexes and to transrepress inflammatory genes [Oshima et al., *J. Biol. Chem.* 279, 29551-29777 (2004); Pascual et al., *Nature* 437, 759-63 (2005); Ghisletti et al., *Mol. Cell.* 25, 57-70 (2007); Ricote and Glass, *Biochim. Biophys. Acta* 1771, 926-935 (2007)]. Additionally, 15-deoxy-$\Delta^{12,14}$-PGJ$_2$ may down-regulate inflammatory genes, through covalent binding to nuclear factor-κB or IκB kinase, without involvement of PPARγ [Straus et al., *Proc. Natl. Acad. Sci. USA* 97, 4844-9 (2000)]. Further discussion of PGD$_2$ metabolites is presented later in this disclosure.

Possible roles for PPARs in tumor development have been topics of great interest among many investigators. Isolation of a PPARγ gene [Zhu et al., *J. Biol. Chem.* 268, 26817-26820 (1993)] and demonstration that PPARγ regulates fat cells [Tontonoz et al., *Genes & Dev.* 8, 1224-1234 (1994)] led to the discovery that adipogenic, thiazolidinedione drugs are potent PPARγ activators [Lehmann et al., *J. Biol. Chem.* 270, 12953-12956 (1995)]. Such drugs include troglitazone, rosiglitazone, and pioglitazone. An epidemiologic link between dietary fat and cancer and the occurrence of high levels of PPARγ in the colon [Mansén et al., *Biochem. Biophys. Res. Commun.* 222, 844-851 (1996); Fajas et al., *J. Biol. Chem.* 272, 18779-18789 (1997)] prompted work on thiazolidinediones in Apc$^{Min/+}$ mice [Lefebvre et al., *Nat. Med.* 4, 1053-1057 (1998); Saez et al., *Nat. Med.* 4, 1058-1061 (1998)]. Effects on colon cancer cell lines have also been examined [Brockman et al., *Gastroenterology* 115, 1049-1055 (1998); Sarraf et al., *Mol. Cell.* 3, 799-804 (1999)]. However, some results have been inconsistent, possibly due to dose effects [Welch et al., *Proc. Natl. Acad. Sci. USA* 100, 6712-6717 (2003)].

Our finding above (from Example I) that high PGD$_2$ production from transgenic H-PGDS reduces tumors in Apc$^{Min/+}$ mice, coupled with the ability of PGD$_2$ and/or metabolites to bind to PPARγ and the potential for ligand-bound PPARγ to transrepress inflammatory genes, led to experiments with L-PGDS transgenic mice in Example II, to obtain further information on tumor suppression involving PGD$_2$.

Table 3 shows that Apc$^{Min/+}$ mice with L-PGDS transgenes tended to have roughly 35% fewer tumors than did controls (medians were 114 versus 180, respectively, for total adenomas; P=0.024, uncorrected; P=0.048, with Bonferroni correction; Table 3A). Tumor suppression by transgenic L-PGDS appeared to mainly involve large adenomas. Median numbers of large adenomas were 50 for L-PGDS transgenic mice versus 83 for controls (P=0.0062, uncorrected; P=0.012, with Bonferroni correction; Table 3C). These differences were also reflected in the ratio of the average number of tumors in L-PGDS transgenic mice to the average number of tumors in controls. Ratios were 0.65 (95% CI 0.44-0.96) for total adenomas and 0.53 (95% CI 0.33-0.85) for large adenomas. Thus, there is evidence that transgenic L-PGDS suppressed tumors in Apc$^{Min/+}$ mice.

TABLE 3

Adenomas in Apc$^{Min/+}$ mice with L-PGDS transgenes, with and without heterozygous Pparγ knockouts A. Total number of adenomas in the entire intestine (P = 0.073†)

|  | Mice without Pparγ KO | | Mice with Pparγ KO | |
| --- | --- | --- | --- | --- |
|  | L-PGDS TG | Control | L-PGDS TG | Control |
| Median | 114 | 180 | 152 | 188 |
| Range | 24-424 | 19-500 | 34-628 | 43-686 |
| No. of mice | 22 | 37 | 18 | 29 |
| P-value‡ | 0.024 | | 0.27 | |
| Ratio (95% CI)‖ | 0.65 (0.44-0.96) | | 0.80 (0.55-1.16) | |

B. Number of small§ adenomas in the entire intestine (P = 0.35†)

|  | Mice without Pparγ KO | | Mice with Pparγ KO | |
| --- | --- | --- | --- | --- |
|  | L-PGDS TG | Control | L-PGDS TG | Control |
| Median | 70 | 97 | 92 | 101 |
| Range | 11-247 | 16-342 | 23-331 | 23-354 |
| No. of mice | 22 | 37 | 18 | 29 |
| P-value‡ | 0.19 | | 0.61 | |
| Ratio (95% CI)‖ | 0.77 (0.52-1.12) | | 0.85 (0.57-1.26) | |

C. Number of large§ adenomas in the entire intestine (P = 0.015†)

|  | Mice without Pparγ KO | | Mice with Pparγ KO | |
| --- | --- | --- | --- | --- |
|  | L-PGDS TG | Control | L-PGDS TG | Control |
| Median | 50 | 83 | 68 | 88 |
| Range | 8-190 | 3-267 | 11-297 | 20-332 |
| No. of mice | 22 | 37 | 18 | 29 |
| P-value‡ | 0.0062 | | 0.08 | |
| Ratio (95% CI)‖ | 0.53 (0.33-0.85) | | 0.71 (0.47-1.06) | |

D. Total number of adenomas in the colon (P = 0.49†)

|  | Mice without Pparγ KO | | Mice with Pparγ KO | |
| --- | --- | --- | --- | --- |
|  | L-PGDS TG | Control | L-PGDS TG | Control |
| Median | 4 | 4 | 3 | 4 |
| Range | 0-15 | 0-26 | 0-12 | 1-30 |
| No. of mice | 22 | 37 | 18 | 29 |
| P-value‡ | 0.60 | | 0.23 | |
| Ratio (95% CI)‖ | 0.75 (0.42-1.35) | | 0.69 (0.41-1.16) | |

*We counted adenomas histologically at 14 weeks of age in 24 Swiss roll sections spaced 150 μm apart. L-PGDS TG indicates mice carrying an L-PGDS transgene. Pparγ KO indicates heterozygosity for a Pparγ knockout mutation. Data for parts A-C are plotted in FIGS. 8A-8C.
†The P-value refers to comparison among all four groups by use of the Kruskal-Wallis test.
‡The P-values shown are uncorrected and refer to comparison between the indicated genotypes by use of the Mann-Whitney test. To obtain a P-value corrected by the Bonferroni method, multiply the P-value shown by two (number of comparisons among the four groups).
§Small adenomas were defined as those seen in only one section, whereas large adenomas were designated as those with profiles seen in multiple sections (i.e., adenomas >150 μm in diameter).
‖Ratio of the mean number of adenomas in L-PGDS transgenic mice to the mean number of adenomas in controls, and 95% confidence intervals.

Without L-PGDS transgenes, the numbers of tumors—total, small, or large—in Pparγ knockout mice were comparable to numbers in mice without Pparγ knockouts (Table 3; see the two columns labeled "Control"). Thus, heterozygous Pparγ knockouts alone did not increase tumors in Apc$^{Min/+}$ mice. To further analyze a role for Pparγ in tumor suppression, we next hypothesized that if PPARγ takes part in the inhibition of tumors by PGD$_2$, then knockout of a Pparγ gene may diminish the tumor-suppressing effect of transgenic L-PGDS.

To determine the influence of both L-PGDS excess and Pparγ deficiency, we produced mice with L-PGDS transgenes and heterozygous Pparγ knockouts. Apc$^{Min/+}$ mice with both L-PGDS transgenes and Pparγ knockouts tended to have an intermediate number of tumors—less than in controls but more than in L-PGDS transgenic mice without Pparγ knockouts. For example, going by median numbers, there were 114 total adenomas for L-PGDS transgenes alone, 188 for Pparγ knockouts alone, and 152 when both mutations were present (Table 3A). Correspondingly, ratios of the average number of tumors in L-PGDS transgenic mice to the average number in controls were: 0.80 (95% CI 0.55-1.16) for total adenomas and 0.71 (95% CI 0.47-1.06) for large adenomas (compare to ratios above for mice without Pparγ knockouts, i.e., 0.65 and 0.53, respectively). None of the changes in Pparγ knockout mice were statistically significant, indicating possible loss or blunting of the L-PGDS protective effect in Pparγ knockout mice. Such blunting or loss of the L-PGDS protective effect is compatible with a role for PPARγ in tumor suppression by PGD2.

Figures 8A, 8B, 8C:
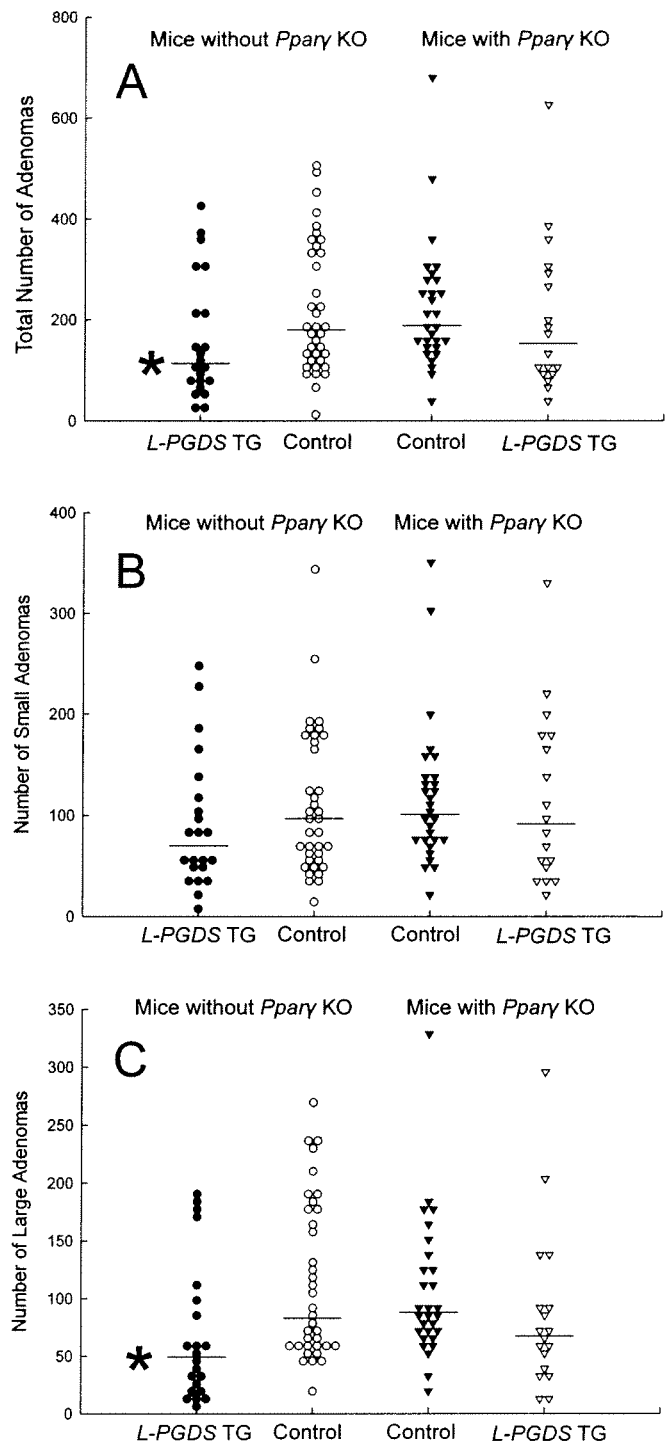
FIG. 8A represents numbers of all adenomas scored in the entire intestine of L-PGDS transgenic mice and controls, with and without heterozygous knockout of the peroxisome proliferator-activated receptor γ (Ppary) gene.
FIG. 8B represents numbers of small adenomas (less than ~150-300 μm in size) scored in the entire intestine of L-PGDS transgenic mice and controls, with and without heterozygous knockout of the Ppary gene.
FIG. 8C represents numbers of large adenomas (greater than ~150-300 μm in size) scored in the entire intestine of L-PGDS transgenic mice and controls, with and without heterozygous knockout of the Ppary gene.
Figures 9A, 9B, 9C, 9D:
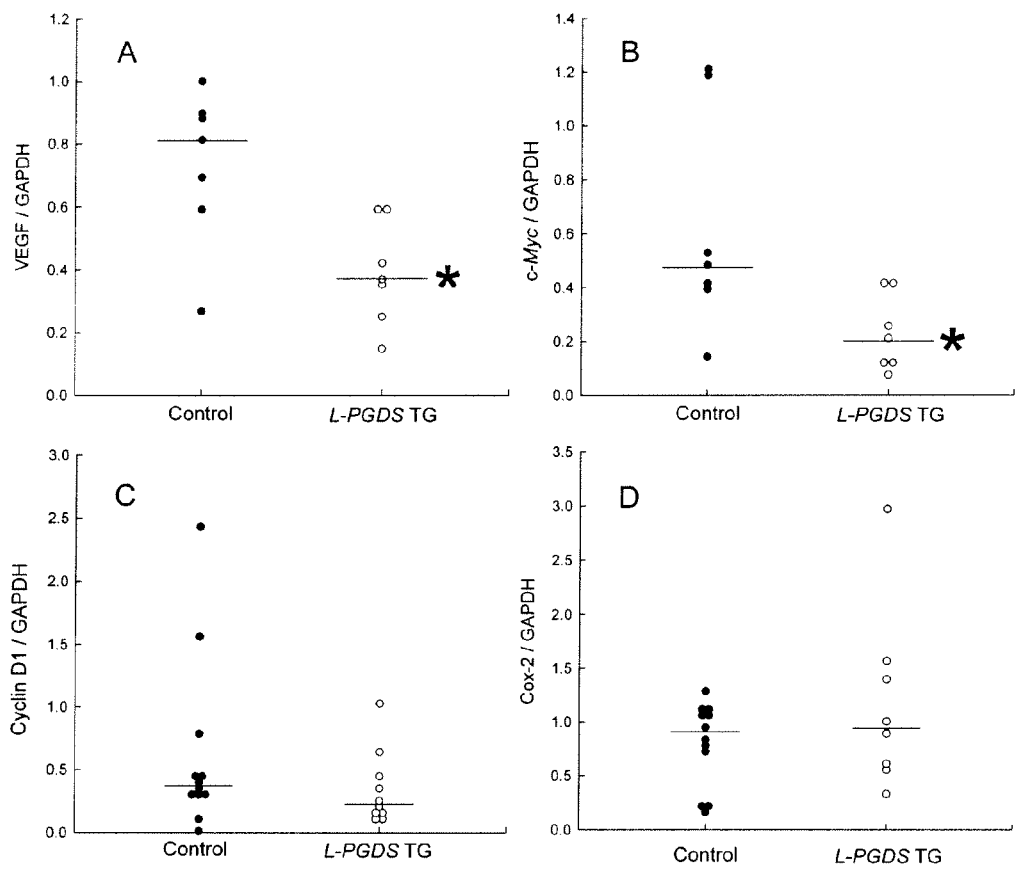
FIG. 9A represents relative expression of vascular endothelial growth factor (VEGF) in the colon of Apc$^{Min/+}$ mice, with and without L-PGDS transgenes.
FIG. 9B represents the relative expression of the c-Myc oncogene in the colon of Apc$^{Min/+}$ mice, with and without L-PGDS transgenes.
FIG. 9C represents the relative expression of cyclin D1 (C) in the colon of Apc$^{Min/+}$ mice, with and without L-PGDS transgenes.
FIG. 9D represents the relative expression of cyclo-oxygenase-2 (Cox-2) in the colon of Apc$^{Min/+}$ mice, with and without L-PGDS transgenes.

Numbers of adenomas in the intestines of Apc$^{Min/+}$ mice with L-PGDS transgenes, with and without heterozygous Pparγ knockout mutations, are illustrated in FIGS. 8A-8C. There were statistically significant reductions in the total numbers of adenomas and in the numbers of large adenomas in L-PGDS transgenic mice without Pparγ knockouts. See Table 3 for median values, ranges, number of mice, P-values, and ratios of numbers of adenomas in L-PGDS transgenic mice to numbers of adenomas in controls. In the figures, L-PGDS TG indicates L-PGDS transgenic mice, and Pparγ KO indicates heterozygous Pparγ knockout mice. Horizontal bars indicate medians. An asterisk (*) indicates a statistically significant difference (P<0.05) between the indicated genotype and controls. FIG. 8A shows the numbers of adenomas in the entire intestine of L-PGDS transgenic mice, heterozygous Pparγ knockout mice, and controls. FIG. 8B shows the numbers of small adenomas (i.e., adenomas less than 150-300 μm in size) in the entire intestine of L-PGDS transgenic mice, heterozygous Pparγ knockout mice, and controls. FIG. 8C shows the numbers of large adenomas (i.e., adenomas greater than 150-300 μm in size) in the entire intestine of L-PGDS transgenic mice, heterozygous Pparγ knockout mice, and controls.

Because prostaglandins take part in control of inflammatory genes that are involved in cell proliferation, we measured colon mRNA levels for a series of such inflammatory genes: vascular endothelial growth factor (VEGF), c-Myc, cyclin D1, and Cox-2. mRNA was prepared from colon tissue, and expression levels of these genes were quantitated relative to mRNA for endogenous mouse glyceraldehyde-3-phosphate dehydrogenase (GAPDH). FIGS. 9A-9D show relative expression of VEGF (FIG. 9A), c-Myc (FIG. 9B), cyclin D1 (FIG. 9C), and Cox-2 (FIG. 9D) in the colon of Apc$^{Min/+}$ mice with and without L-PGDS transgenes. Plotted points show triplicate measurements in different mice. Horizontal bars show medians. Median values for control and L-PGDS transgenic mice (respectively) were: for VEGF, 0.81 and 0.37 (P=0.022); for c-Myc, 0.47 and 0.20 (P=0.041); for cyclin D1, 0.37 and 0.23 (P=0.31); and for Cox-2, 0.91 and 0.94 (P=0.46). An asterisk (*) indicates a statistically significant difference (P<0.05) between mRNA levels for the indicated genotype versus controls. Median levels for VEGF and c-Myc were reduced by more than 50% in Apc$^{Min/+}$ mice with transgenic L-PGDS (P<0.05).

VEGF and c-Myc are known to promote tumors in Apc$^{Min/+}$ mice. For example, loss of Myc restored the normal appearance of intestinal crypts in mice with intestine-specific knockout of the Apc gene [Sansom et al., Nature 446, 676-679 (2007)]. Morphologic changes included two-fold fewer cells per crypt and mitoses per crypt. Goodlad et al. [*Carcinogenesis* 27, 2133-2139 (2006)] administered by gavage an inhibitor of VEGF receptor-2 to six- or 10-week-old Apc$^{Min/+}$ mice for 28 days and then scored adenomas. The treatment reduced adenoma number and size in the younger mice, and adenoma size in the older animals. Thus, the observed reduction in c-Myc and VEGF expression in the colon is compatible with tumor suppression in the experiments shown.

Median sizes of adenomas were somewhat smaller in L-PGDS transgenic mice, but the differences were not statistically significant. Finally, there was no detectable effect of L-PGDS on colon adenomas (see Table 3D), possibly due to the smaller number of tumors that occur in the colon.

To summarize the results shown in Table 3 and FIGS. 8A-9D, there were roughly 35% fewer adenomas in Apc$^{Min/+}$ mice with transgenic L-PGDS (e.g., medians of 114 for L-PDGS transgenic mice, versus 180 for controls; P=0.048). L-PGDS thus reproduces the tumor preventive effect documented with H-PGDS as illustrated in Example I even though L-PGDS is not part of the normal physiologic milieu of the gut. Transgenic L-PGDS was also associated with lower colon expression of vascular endothelial growth factor (VEGF) and c-Myc. Heterozygous Pparγ knockouts alone did not increase the number of tumors in Apc$^{Min/+}$ mice. However, tumor suppression by L-PGDS was blunted in Pparγ knockout mice, judging by ratios of numbers of adenomas in L-PGDS transgenic mice to numbers in controls—0.65 for mice without Pparγ knockouts (95% CI 0.44-0.96) versus 0.80 for mice with Pparγ knockouts (95% CI 0.55-1.16). Examples I and II thus establish a role for augmenting PGD, production as a means to suppress and/or inhibit tumor growth. Further, the results support an interpretation that PGD$_2$ metabolites may down-regulate inflammatory and cell proliferation genes, possibly through interaction with PPARγ.

Mice prone to intestinal polyposis have been widely used to study prostaglandin effects on adenomas. Effects of disruption of genes in the prostaglandin E pathway support a conclusion that PGE$_2$ promotes tumors. In the work documented here, knockouts of two types of prostaglandin D synthase, as well as transgenic mice with high levels of human H-PGDS or L-PGDS, were analyzed. These genes represent the only known enzymes in the PGD2 pathway from prostaglandin The intestinal mucosa contains prostaglandin H synthase 2 (PTGS2, or Cox-2), mostly in stromal fibroblasts and endothelial cells. Colon adenomas and carcinomas also have high levels of inducible microsomal prostaglandin E synthase. This enzyme produces PGE2 and stains readily in epithelial cells of colorectal tumors. Thus, prostaglandin production in various cell types, such as, but not limited to, fibroblasts, epithelial cells, and macrophages, influences adenoma growth. For example, PGE$_2$ made in epithelial cells, or imported there from stromal cells, appears to promote adenomas. In an opposite effect, the results here indicate that H-PGDS made in macrophages may suppress adenomas.

A macrophage role in tumorigenesis has been recognized, and it is further known that tumor-associated macrophages have both stimulating and inhibitory influences. Stimulating factors produced by macrophages include nitric oxide synthase, vascular endothelial growth factors, matrix enzymes (e.g., metalloproteinases), and other cytokines (e.g., tumor necrosis factor α, interleukin-1α).

Macrophage involvement in tumor development was specifically observed when investigators produced transgenic mice with high expression of PTGS2 and microsomal prostaglandin E synthase in the stomach epithelium [Oshima et al., *EMBO J.* 23, 1669-1678 (2004)]. The mice had heavy macrophage infiltration and large, benign tumors in the stomach. Treating the mice with a PTGS2 inhibitor prevented both macrophage infiltration and tumors. It was therefore proposed that PGE2 caused macrophage infiltration leading to tumors when macrophages were activated by gastric flora.

Biochemically, $PGD_2$ converts without enzymes to $PGD_2$ [also known as 9-deoxy-$\Delta^9$-$PGD_2$; Fukushima et al., *Biochem. Biophys. Res. Commun.* 109, 626-633 (1982); Fitzpatrick and Wynalda, *J. Biol. Chem.* 258, 11713-11718 (1983)], which can further dehydrate to $\Delta^{12}$-$PGJ_2$ and 15-deoxy-$\Delta^{12,14}$-$PGJ_2$ [Hirata et al., *J. Biol. Chem.* 263, 16619-16625 (1988); Forman et al., *Cell* 83, 803-812 (1995); Kliewer et al., *Cell* 83, 813-819 (1995)]. These compounds—$PGD_2$, $PGD_2$, $\Delta^{12}$-$PGJ_2$, and 15-deoxy-$\Delta^{12,14}$-$PGJ_2$—were the first naturally occurring PPARγ ligands to be recognized, through their ability to activate PPARγ response elements [Forman et al., *Cell* 83, 803-812 (1995)] and promote differentiation of fibroblasts to adipocytes [Kliewer et al., *Cell* 83, 813-819 (1995)]. Such $PGD_2$ metabolites inhibited growth of cultured cells and Ehrlich ascites tumors, in early reports [Fukushima et al., *Biochem. Biophys. Res. Commun.* 109, 626-633 (1982); Kato et al., *Cancer Res.* 46, 3538-3542 (1986); Narumiya et al., *J. Pharmacol. Exp. Ther.* 242, 306-311 (1987)]. In addition, 15-deoxy-$\Delta^{12,14}$-$PGJ_2$ is also believed to form covalent attachments to Keap1 (Kelch-like ECH-associated protein 1) and IκB kinase, which can act as signaling factors for tumor inhibition [Yu et al., *J. Biol. Chem.* 281, 26245-26252 (2006)].

Evidence has been found for blunting of macrophage activation by $PGD_2$ metabolites [Ricote et. al., *Nature* 391, 79-82 (1998)]. Activated peritoneal macrophages have more peroxisome proliferator-activated receptor γ (PPARγ), compared to the resting macrophages in bone marrow. Activated macrophages, however, treated with 15-deoxy-$\Delta^{12,14}$-$PGJ_2$ (a compound described in the paragraph above) were found to have properties of resting macrophages, such as low inducibility of nitric oxide synthetase and little or no gelatinase B (matrix metalloproteinase 9). Thus, one conclusion is that PPARγ may be a negative regulator of macrophage activation in response to $PGD_2$ metabolites.

Shibata et al. [*J. Biol. Chem.* 277, 10459-10466 (2002)] detected 15-deoxy-$\Delta^{12,14}$-$PGJ_2$ in cultured macrophages by immunohistochemistry. However, Bell-Parikh et al. found only minute amounts of this prostaglandin in cells [*J. Clin. Invest.* 112, 945-955 (2003)]. For example, culture medium from 3T3-L1 fibroblasts had roughly 2 pM concentrations of the compound, compared to 3 nM for $PGE_2$ and the >2.5 μM level needed to activate PPARγ. Thus, 15-deoxy-$\Delta^{12,14}$-PGJ, may not be physiologically important. Roles of other potential PPARγ ligands derived from $PGD_2$ (such as $PGJ_2$ and $\Delta^{12}$-$PGJ_2$) remain to be defined.

As an alternative mechanism, transgenic H-PGDS could potentially inhibit tumors by shifting conversion of prostaglandin Ft, away from $PGE_2$ (i.e., lowering $PGE_2$ levels in the intestine). In contrast, knockout of H-Pgds could potentially promote tumor growth by favoring conversion of $PGH_2$ to $PGE_2$ (i.e., raising $PGE_2$ levels in the intestine). $PGD_2$ represents 6% of total prostaglandins in macrophages, compared to 63% for $PGE_2$ [Trebino et al., *J. Biol. Chem.* 280, 16579-16585 (2005)].

As illustrated in FIGS. 3A-3B, H-PGDS transgenic mice tended to have more 11β-$PGF_{2\alpha}$ and less PGE-M in the urine, compared to wild-type mice. The results are compatible with higher $PGD_2$ production and lower $PGE_2$ production. However, the results were not statistically significant, due to wide variability in urine prostaglandin levels. It is known that very high $PGD_2$ production in transgenic mice requires cell activation by, for example, pain, bacterial lipopolysaccharides, ethanol, or other stimuli [Pinzar et al., *Proc. Natl. Acad. Sci. USA* 97, 4903-4907 (2000)]. Specifically, Pinzar et al. found that unstimulated L-PGDS transgenic mice had only 1.5-fold more $PGD_2$ in the brain than did wild-type controls. However, pain stimulation by tail clipping, for example, led to 17-fold more brain $PGD_2$ in one of the transgenic lines (B7). The mice used in Examples I and II were not exposed to pain or other stimuli. Alternatively, it is possible that 24-hour urinary prostaglandins do not closely reflect $PGD_2$ levels in the intestines.

Other investigators have shown that null mutations of the prostaglandin D receptor (DP1) do not raise numbers of aberrant crypt foci in mice treated with the colon carcinogen, azoxymethane. Therefore, DP1 may not be part of the $PGD_2$ effect documented here. However, there have been no studies of the DP1 receptor in $Apc^{Min/+}$ mice. $PGD_2$ action through other prostanoid receptors, such as CRTH2 (chemoattractant receptor-homologous molecule expressed on T helper type-2 cells), may also be possible [Hirai et al., *J. Exp. Med.* 193, 255-261 (2001)].

In summary, gene knockouts of hematopoietic prostaglandin D synthase led to more adenomas in $Apc^{Min/+}$ mice. Moreover, mice with higher prostaglandin D synthase enzyme levels from transgenic human H-PGDS or L-PGDS—expressed in all cells—had fewer adenomas. In the intestinal mucosa, H-Pgds was detected mainly in macrophages and mononuclear cells. High $PGD_2$ production from transgenic L-PGDS was also associated with lower colon expression of vascular endothelial growth factor (VEGF) and c-Mvc, which are tumor promoting growth factors. The results support the conclusion that high production of PGD2, or metabolites can inhibit and/or prevent the growth of intestinal adenomas.

Introduction to the Examples

The results above for $Apc^{Min/+}$ mice may be achieved according to techniques described in Examples I and II. It is contemplated however, that modifications of the techniques described herein, or other techniques, may be used to produce similar effects on $PGD_2$ production. Therefore, the methods and techniques described in Examples I and II are provided in an exemplary but not in a restrictive sense.

Example III gives details on discovery, characterization, and identification of the Val187Ile H-PGDS variant in humans. The genetically engineered Val187Ile form of H-PGDS represents further embodiments for raising $PGD_2$ production in the body or for identifying individuals with a genetic predisposition for augmented $PGD_2$ production in the body.

Example I

Manipulation of $PGD_2$ in H-Pgds Knockout and H-PGDS Transgenic Mice a. Mouse Strains C57BL/6J, FVB/NJ, and $Apc^{Min/+}$ (stock no. 002020) mice from the Jackson Laboratory (Bar Harbor, Me.) were used. L-Pgds knockout mice were produced as described [Eguchi et al., *Proc. Natl. Acad. Sci. USA* 96, 726-730 (1999)]. Production of H-Pgds knockout and H-PGDS transgenic mice was at Osaka Bioscience Institute and the Japan Tobacco Inc. Pharmaceutical Frontier Research Laboratories, prior to the work described herein. All animals were fed Purina lab rodent diet (LabDiet 5001) ad libitum.

The exon 2 deletion in the H-Pgds knockout mice used in Example I could theoretically lead to a truncated protein, unrecognized by the antibody, which might have a dominant negative effect on the H-Pgds dimer. However, protein translation from the next available, in-frame ATG (methionine 99 of exon 4) would leave out part of the dimer interface, including three important aspartic acid residues (93, 96, and 97). Furthermore, it is known that mast cells from homozygous knockout mice did not contain detectable H-Pgds mRNA. Therefore, an altered enzyme in H-Pgds$^{+/-}$ mice is unlikely.

b. Mouse Breeding

Apc$^{Min/+}$ males were crossed with heterozygous H-Pgds$^{+/-}$ females to produce Apc$^{Min/+}$ H-Pgds$^{+/-}$ offspring. Apc$^{Min/+}$ H-Pgds$^{+/-}$ males were bred with H-Pgds$^{+/-}$ or H-Pgds$^{-/-}$ females to produce Apc$^{Min/+}$ H-Pgds$^{-/-}$ mice. Apc$^{Min/+}$ L-Pgds$^{-/-}$ mice were produced by the same strategy.

Male H-PGDS transgenic mice (strain FVB/N) were bred with C57BL/6 females to produce transgenic mice on a mixed C57BL/6×FVB/N background. Similarly, C57BL/6 Apc$^{Min/+}$ males were bred with FVB/N females to produce mixed Apc$^{Min/+}$ mice. The progeny were then intercrossed to produce H-PGDS transgenic Apc$^{Min/+}$ mice on a mixed background.

Genotyping

Genotyping of mice was done by use of PCR. DNA templates were 1 mm punches of dried blood on blotter paper (No. 903 paper; Whatman Schleicher and Schuell; Florham Park, N.J.). Drops of blood from tail segments were collected at 10 days and when the mice were sacrificed. Both blood specimens were genotyped. For H-PGDS transgenic mice with Apc$^{Min/+}$, DNA from 10 μm sections of the paraffin blocks containing coiled intestines was also used. Each PCR was in a total volume of 15 μl. Detection of PCR products was on agarose gels stained with ethidium bromide. PCR primers are shown in Table 3.

d. Urine Prostaglandins

Mice were housed mice individually in metabolic cages, in order to obtain urine. Urine was collected during the day and overnight for a 24-hour period, then centrifuged to remove debris, and frozen at −80° C. until ready for assay. Determinations of 11β-PGF$_{2+}$ and 9,15-dioxo-11α-hydroxy-2,3,4,5-tetranor-prostan-1,20-dioic acid (PGE-M) were done by enzyme immunoassay kits (Cayman; Ann Arbor, Mich.). Urine creatinine was quantitated by use of the Jaffe alkaline picrate reaction in an autoanalyzer. The urine data (pg of prostaglandin per mg of creatinine) were transformed to their logarithms (base 10). Differences in urine prostaglandin excretion between wild-type and transgenic mice were assessed by use of mixed model analysis of variance, in order to account for multiple and varying numbers of urine samples per mouse.

e. Intestinal Histopathology

Mice were sacrificed at 14 weeks, and the intestine was immediately removed in one piece and placed in a glass dish with Ringer solution. The interior of the intestine was flushed with Ringer solution through an 18-gauge needle then flattened on Whatman 3mM paper, opened lengthwise, and fixed in buffered formalin for 2-4 hours. The fixed intestine was coiled like a Swiss roll (inside out) around a wooden stick, the stick removed, and then the coil was placed in an embedding cassette. Specimens were embedded in paraffin, sectioned (4 μm thickness), mounted on slides (Snowcoat X-tra; Surgipath; Richmond, Ill.), and stained with hematoxylin and eosin. Sections were examined microscopically to identify and count adenomas (40-100× magnification or higher), without knowledge of genotypes. Adenomas were measured by use of an eyepiece graticule on a Leica MZ6 dissecting microscope.

For H-Pgds and L-Pgds knockout mice, 18 sections spaced 240-260 μm apart were examined. For H-PGDS transgenic mice, 24 sections spaced approximately 150 μm apart were examined. More sections were examined for transgenic mice than for knockout mice, in case there were substantially fewer

TABLE 3

PCR primer pairs, product sizes (bp), and annealing temperatures (Tm, ° C.)

| Gene | Primer Pair | Primer sequence | Size (bp) | Temp (Tm, ° C.) |
|---|---|---|---|---|
| Apc$^{min}$ | APCMIN-TL1 (wild-type) | 5'-CGTTCTGAGAAAGACAGAAGTTT-3' | 262 | 62 |
| | APCMIN-R1 (common) | 5'-AGTGTGTGTGGGAGGCAG-3' | | |
| | APCMIN-AL1 (mutant) | 5'-CGTTCTGAGAAAGACAGAAGTTA-3' | 262 | 62 |
| | APCMIN-R1 (common) | 5'-AGTGTGTGTGGGAGGCAG-3' | | |
| Mouse H-Pgds | F1 (wild-type) | 5'-GAGTTGCTGCATCTGACCTTTTC-3' | 773 | 65 |
| | R1 (wild-type) | 5'-TAGCGAATAATTTCGGCTCTTCC-3' | | |
| | F2 (KO) | 5'-AAGATCGTCTTGTTGCGTACGCT-3' | 900 | 55 |
| | Neo (KO) | 5'-GTCCAGATCATCCTGATCGAC-3' | | |
| Mouse L-Pgds | L-maeF8 (wild-type) | 5'-TGTCAGGAATGTGGTATGCTC-3' | 397 | 55 |
| | Ex2R2 (wild-type) | 5'-TAGAGGTGAGATTGAGGCCGC-3' | | |
| | L-Ex4F8 (wild-type) | 5'-TGGAGGCCAACTATGACGAGT-3' | 972 | 55 |
| | L-PGDS#4 (wild-type) | 5'-TCACTTGGATGCGTGTGCTTGGGAGCTGT-3' | | |
| | L-maeF8 (knockout) | 5'-TGTCAGGAATGTGGTATGCTC-3' | 950 | 55 |
| | Neo (knockout) | 5'-GTCCAGATCATCCTGATCGAC-3' | | |
| | Neo' (knockout) | 5'-ATCGCCTTCTATCGCCTTCTTGACAGAT-3' | 350 | 55 |
| | L-PGDS#4 (knockout) | 5'-TCACTTGGATGCGTGTGCTTGGGAGCTGT-3' | | |
| Human H-PGDS transgene | CMV-F1 | 5'-GGAGTTCCGCGTTACATAACTTACG-3' | 250 | 50 |
| | CMV-R1 | 5'-GGTCATGTACTGGGCATAATCCCAG-3' | | | adenomas due to the transgene or to the mixed genetic background of the mice. Use of sections spaced 150 μm apart allows detection of most small adenomas, which are usually ≥100 μm in diameter (see FIGS. 5A-5F for the size range). Numbers of adenomas in transgenic mice are not directly comparable to numbers in the knockout mice, due to these differences in methods.

Sections of the same adenoma may be recognized at different levels in the block, but each adenoma was counted only once. A color coding procedure was used to avoid overcounting. Specifically, each slide had two sections, mounted left to right in the order of cutting. All adenoma profiles were first marked with a red ink dot. All slides were then examined again to compare the left section to the right section. Profiles were marked with a black dot, if the same adenoma was represented on both the left and right section of the same slide. All slides were then examined a third time to compare adenoma profiles in the right section of each slide to the left section of the next consecutive slide. Profiles were marked with a blue dot, if the adenoma was represented on both the right section of a slide and on the left section of the next consecutive slide. Thus, all adenoma profiles were marked with either one red dot, two dots (either red/black or red/blue), or three dots (red/black/blue). For adenoma scoring, we counted the number of "red" and "red/black" adenoma profiles on the right section of each slide and the "red" and "red/blue" adenoma profiles on the left section of each slide. The counts were added to obtain the total number of adenomas per mouse.

10% of the intestines were selected at random for re-counting adenomas, again without knowledge of genotypes. Average deviations in counts were 1.4 adenomas for the entire intestine. Slides were also chosen at random for independent re-review.

For statistical analyses in Example I, the numbers of adenomas were transformed to their logarithms (base 10) for statistical analyses by both analysis of variance with Dunnett's method and nonparametric tests (Mann-Whitney with Bonferroni corrections).

f. Immunohistochemistry

Deparaffinized sections were treated with 10 mM Tris-HCl at pH 9.5 (45 minutes, 80° C.) for unmasking, followed by 0.3% $H_2O_2$ in methanol to inhibit endogenous peroxidases (15 minutes, room temperature) and 20% normal goat serum in phosphate buffered saline for blocking (30 minutes, room temperature). Next, sections were treated with 0.1% Triton X-100 (10 minutes, room temperature). Then, for staining, either a rat anti-mouse H-Pgds monoclonal antibody (1:100 dilution) or a rabbit anti-mouse H-Pgds polyclonal antibody (1:200 dilution) in PBS (overnight; both from Cayman) was used. Signal detection was with biotinylated anti-rat or anti-rabbit IgG, respectively (Vector Laboratories; Burlingame, Calif.), followed by avidin-biotin-peroxidase complexes and diaminobenzidine as the chromogen. The avidin-biotin-peroxidase reaction was done in 0.35 M NaCl, in order to prevent nonspecific avidin binding to mast cells.

Example II

Manipulation of $PGD_2$ mL-PGDS Transgenic Mice a. Mouse Strains

C57BL/6, FVB/N, and $Apc^{Min/+}$ (stock no. 002020) mice came from the Jackson Laboratory (Bar Harbor, Me.), as did mice carrying the Cre transgene under the control of the adenovirus EIIa promoter [Tg(EIIa-Cre) C5379Lmgd/J; stock no. 003314; Lakso et al. 1996]. Mice in which exon 2 of the Pparγ gene is flanked by loxP sites ($Pparγ^{flox/flox}$ FVB/N mice) were obtained from the National Cancer Institute [Bethesda, Md.; Akiyama et al., *Mol. Cell. Biol.* 22, 2607-2619 (2002)].

The L-PGDS transgenic mouse strain used (line B20 in the FVB/N strain) was one of the lines described in Pinzar et al. [*Proc. Natl. Acad. Sci. USA* 97, 4903-4907 (2000)]. The human L-PGDS transgene in these mice is expressed in all cells, due to constitutive control by the cytomegalovirus immediate early enhancer, the chicken β-actin promoter, and the rabbit β-globin polyadenylation signal. Basal tissue (brain) levels of PGD2 were 1.5-fold higher than in wild-type mice. PGD2 rose another five-fold upon stimulation by tail clipping for DNA collection, and mice became somnolent. PGE2 levels were judged to be unchanged from wild-type levels in these mice. Furthermore, the L-PGDS transgenic mouse line used in this example produced more eosinophilia in a bronchial asthma model, compared to H-PGDS transgenic lines [Fujitani et al., *J. Immunol.* 168, 443-449 (2002)].

For Pparγ knockouts, we used a mouse mutant with deletion of exon 2 [Akiyama et al., *Mol. Cell. Biol.* 22, 2607-2619 (2002)]. Heterozygotes have less Pparγ protein in colonic epithelium and two- to three-fold more tumors and shorter lifespan when exposed to azoxymethane. However, the knockout was not associated with changes in occurrence of adenomas in $Apc^{1638N/+}$ mice, a strain with attenuated tumor growth [Girnun et al., *Proc. Natl. Acad. Sci. USA* 99, 13771-13776 (2002)].

b. Mouse Breeding

We crossed $Pparγ^{flox/flox}$ mice with Tg(EIIa-Cre) mice and genotyped offspring to identify heterozygous mice lacking exon 2 of the Pparγ gene ($Pparγ^{+/-}$ mice). We then crossed female $Pparγ^{+/-}$ mice on an FVB/N background with male $Apc^{Min/+}$ mice on a C57BL/6 background to produce $Apc^{Min/+}$ $Pparγ^{+/-}$, $Apc^{Min/+}$, and $Pparγ^{+/-}$ mice, all on a mixed background. Similarly, we bred L-PGDS transgenic FVB/N males with C57BL/6 females to produce transgenic mice on a mixed C57BL/6×FVB/N background. We intercrossed these offspring to obtain animals (including littermates) for experiments described.

c. Genotyping

Genotyping of mice was done by use of PCR, as described above for Example I. PCR primers are shown in Table 3.

TABLE 3

PCR primer pairs, product sizes (bp), and annealing temperatures (Tm, ° C.)

| Gene | Primer Pair | Primer sequence | Size (bp) | Temp (Tm, ° C.) |
|---|---|---|---|---|
| $Apc^{Min}$ | APCMIN-TL1 (wild-type) | 5'-CGTTCTGAGAAAGACAGAAGTTT-3' | 262 | 62 |
| | APCMIN-R1 (common) | 5'-AGTGTGTGTGGGAGGCAG-3' | | |

TABLE 3-continued

PCR primer pairs, product sizes (bp), and annealing temperatures (Tm, ° C.)

| Gene | Primer Pair | Primer sequence | Size (bp) | Temp (Tm, ° C.) |
|---|---|---|---|---|
| | APCMIN-AL1 (mutant) | 5'-CGTTCTGAGAAAGACAGAAGTTA-3' | 262 | 62 |
| | APCMIN-R1 (common) | 5'-AGTGTGTGTGGGAGGCAG-3' | | |
| Human L-PGDS transgene | h-LPGDS f2 TG<br>m-LPGDS r | 5'-CGAGCTGGCTCCAGGAGAAGAAGGC-3'<br>5'-GCTGAGAGGGTGGCCATGCGGAAG-3' | 300 | 71.5 |
| Mouse Pparγ wild-type | 2F<br>1R | 5'-CTCCAATGTTCTCAAACTTAC-3'<br>5'-GATGAGTCATGTAAGTTGACC-3' | 250 | 60 |
| Mouse Pparγ floxed allele | 2F<br>1R | 5'-CTCCAATGTTCTCAAACTTAC-3'<br>5'-GATGAGTCATGTAAGTTGACC-3' | 285 | 60 |
| Mouse Pparγ null allele | 2F<br>H5 | 5'-CTCCAATGTTCTCAAACTTAC-3'<br>5'-GTATTCTATGGCTTCCAGTGC-3' | 450 | 60 | d. Intestinal Histopathology

Mice were sacrificed at 14 weeks. Intestines were removed, embedded in paraffin, sectioned, stained, and microscopically examined as described in Example I for H-PGDS transgenic mice. We examined 24 sections spaced approximately 150 µm apart. For analyses involving tumor size, we defined small adenomas as those seen in only one section (i.e., adenomas <150-300 µm in diameter) and designated large adenomas as those with profiles seen in multiple sections (i.e., size >150-300 µm).

Numbers of adenomas were statistically analyzed by non-parametric methods (Kruskal-Wallis tests for comparisons among three or more groups of mice; Mann-Whitney tests with Bonferroni correction for comparisons between two groups of mice).

e. mRNA Analyses

Fresh colon specimens (~100 mg) were placed in RNAlater (Ambion; Austin, Tex.) and frozen at the time of sacrifice. RNA was extracted, purified (RNeasy Lipid Tissue Mini Kit, Qiagen; Germantown, Md.), reverse transcribed to cDNA, and quantitated via RT-PCR. Assays for c-Myc, cyclooxygenase-2 (Cox-2), cyclin D1, glyceraldehyde-3-phosphate dehydrogenase, and vascular endothelial growth factor (VEGF) mRNA were performed with Taqman kits (Applied Biosystems; Foster City, Calif.; Mm00487803_m1, Mm00478374_m1, Mm00432359_m1, Mm99999915_g1, Mm00437304_m1, respectively). P-values for comparisons of mRNA data from L-PGDS transgenic mice versus controls were calculated by the use of the Mann-Whitney method.

Example III

Discovery, Construction, Enhanced Stability, and Genotyping of the Val187Ile Variant of the Human H-PGDS Enzyme a. Identification of Naturally Occurring Human H-PGDS Variants Blood specimens obtained from a large tissue typing laboratory were used as material to search for common H-PGDS variants among people of different ethnic groups. The specimens came from random batches of specimens without identifiers, collected from volunteers between February, 1992, and November, 1993. Most blood specimens were from the Los Angeles area, but the laboratory also received specimens from foreign countries. Volunteers were generally unrelated, between the ages of 18 and 65, and did not have a history of chronic illness, including cancer. There was no duplicate sampling or gender preference. Ethnic groups represented were: African Americans, Chinese (Hong Kong), Filipinos, Hispanics, Asian Indians, Japanese, Koreans, Samoans, and whites.

Further blood specimens came from 82 African American participants in a study on genetic variants of prostaglandin metabolism (conducted between January and August, 2003). Subjects were 19-50 years of age, non-smokers [by history and by urine cotinine levels as measured by commercially available "dipsticks" (NicoMeter; Jant Pharmacal Corp.; Encino, Calif.)], and not recent users of aspirin (14 days) or other nonsteroidal anti-inflammatory drugs (5 days). They were not affected by hypertension, heart conditions, diabetes, kidney problems, ulcer disease, or use of drugs or alcohol.

b. Polymerase Chain Reaction

PCR templates were 1×1 mm squares of dried blood on blotter paper (No. 903 paper; Whatman Schleicher and Schuell). Each PCR contained 40 µM of each deoxynucleotide, 1 µM of each primer, 20 µg ml$^{-1}$ of bovine serum albumin, buffers recommended by Taq polymerase suppliers, and a total volume of 10-40 µl. MgCl$_2$ was optimized for each pair of primers. Heating was done in a Perkin Elmer 9600, Applied Biosystems 9700, or MJ Research PTC-100 thermal cycler [95° C. for 15 min; then the temperature was lowered to 85° C. for 10 min while 0.25 U of Taq polymerase was added; then 26-32 cycles of 94° C. for 30 s, the annealing temperature for 40 s, 72° C. for 60 s; then 72° C. for 5 min]. PCR primers were selected by use of a computer program, with theoretical annealing temperatures matched to within 3-5° C. (see Table 4).

TABLE 4

Oligonucleotide primers used for PCR amplification and DNA sequencing of exons in the human hematopoietic prostaglandin D synthase (H-PGDS) gene

| H-PGDS exon | Name of primer | Primer sequence | Position |
|---|---|---|---|
| 5' primers: | | | |
| 2 | HPGDS-L12 | 5'-GGCATCTCTAGAGGGCTC-3' | 19750543 |
| 3 | HPGDS-L6 | 5'-TGCTTTGTTTTCACGATG-3' | 19733910 |
| 4 | HPGDS-L16 | 5'-TCTTTGAATTTTCAACCATATG-3' | 19724696 |
|   | HPGDS-L7 | 5'-TTCAACCATATGAGTATACTATCTG-3' | 19724686 |
| 5 | HPGDS-L5 | 5'-GATGTTCAATGAGCTGCTCACG-3' | 19718194 |
|   | HPGDS-L8 | 5'-TACTTCCTCCTCAGATCATG-3' | 19718168 |
|   | PGDS-383TL2 | 5'-AATGCGCCTCATCTTAT-3' | 19718069 |
|   | PGDS-383CL2 | 5'-AATGCGCCTCATCTTAC-3' | 19718069 |
| 6 | HPGDS-L9 | 5'-GGAATGCTGATACAGCTACAC-3' | 19715560 |
|   | HPGDS-L13 | 5'-CTACACTTTCTATGTTCAAATGAAA-3' | 19715545 |
|   | HPGDSV187GL | 5'-AGTCCAAGCCATTCCTGCCG-3' | 19715395 |
|   | HPGDSV187AL | 5'-AGTCCAAGCCATTCCTGCCA-3' | 19715395 |
| 3' primers: | | | |
| 2 | HPGDS-R11 | 5'-TTATTTAGTCTGAACTGCTGC-3' | 19750214 |
| 3 | HPGDS-R6 | 5'-TTTGTACTATAGTATGCTATGCTAAA-3' | 19733625 |
| 4 | PGDS-271AR3 | 5'-TCATCCAGAGTGTCCACAAT-3' | 19724554 |
|   | PGDS-271GR3 | 5'-TCATCCAGAGTGTCCACAAC-3' | 19724554 |
|   | HPGDS-R3 | 5'-ATCTTGCTTTTTCTCTGCCCA-3' | 19724495 |
|   | HPGDS-R7 | 5'-CCTAACACAATGTCTGGC-3' | 19724425 |
| 5 | HPGDS-R8 | 5'-TTTATACTTCTATTGGTTTGTCC-3' | 19717937 |
|   | HPGDS-R13 | 5'-TTAACCTTTGTTCTTGCTG-3' | 19717874 |
|   | HPGDS-R11B | 5'-GTTTAACCTTTGTTCTTGCTG-3' | 19717872 |
| 6 | HPGDS-R1 | 5'-GATGCCCCCGAGAAAAACAAACTTG-3' | 19715293 |
|   | HPGDS-R9 | 5'-ATCTGATGAGAGAGATGCC-3' | 19715280 |
|   | HPGDS-R14 | 5'-GTGCAAAGCAAGGTCTGCCTGT-3' | 19715079 |

Notes for Table 4
See sections c through e below for uses of primers for heteroduplex analysis, allele-specific PCR, and DNA sequencing.
"Position" refers to the number in National Center for Biotechnology Information (NCBI) file NT 016354 of the 5' nucleotide of the primer. The positions of the A of the ATG of the initiator methionine and of the G of the TAG stop codon of the H-PGDS gene are 1975084 and 19715335, respectively.

c. Heteroduplex Analysis of H-PGDS Exons

All exons (and their flanking intron regions) of the human H-PGDS gene were screened for variants by use of DNA heteroduplex analysis on specimens from 47 African American and 47 white subjects [Ganguly et al., Proc. Natl. Acad. Sci. USA 90, 10325-10329 (1993); Williams et al., Hum. Molec. Genet. 4, 309-312 (1995)]. PCR conditions were as above, with total volumes of 10 μl and 1 μCi of [α$^{33}$P]dATP (3000 Ci mmol$^{-1}$; ICN Pharmaceuticals; Irvine, Calif.). Primer pairs, annealing temperatures, and sizes of PCR products were: for exon 2, L12 and R11 (53° C.; 329 bp); for exon 3, L6 and R6 (53° C.; 286 bp); for exon 4, L7 and R7 (53° C.; 259 bp); for exon 5, L8 and R8 (52° C.; 232 bp); for exon 6, L9 and R9 (52° C.; 281 bp). Primer sequences are shown in Table 4. After amplification, products were heated to 98° C. for 5 min, incubated at 68° C. for 1 hour to form heteroduplexes, electrophoresed on 10% polyacrylamide gels to separate variant products, and visualized by autoradiography [Lin et al., Pharmacogenet. 8, 269-281 (1998)].

d. DNA Sequencing to Identify H-PGDS Variants

PCR products that showed variation by heteroduplex analysis were treated with exonuclease I and shrimp alkaline phosphatase (United States Biochemical; Cleveland, Ohio) or purified from agarose gels. The treated products were sequenced by use of the Sanger dideoxy method to identify the exact mutations. Sequencing primers were: L5, L6, L7, L8, L9, L12, L13, R1, R3, R6, R7, R8, R9, R11, and R11B (see Table 4). Mutations identified are listed in Table 5.

TABLE 5

Human H-PGDS variants identified by heteroduplex analysis and DNA sequencing

| H-PGDS variant | Gene region | Heterozygote frequency | | Allele frequency (95% confidence interval) | |
|---|---|---|---|---|---|
| | | African Americans | Whites | African Americans | Whites |
| IVS2 + 11 A > C | Intron 2 | 15/47* | 22/47* | 0.80 (0.070-0.087) | 0.64 (0.54-0.73) |
| IVS3 + 13 T > C | Intron 3 | 3/47† | 1/471† | 0.032 (0.007-0.092) | 0.011 (0.00-0.047) |
| c.271 A > G (Ile91Val) | Exon 4 | 12/398‡ | 4/147§ | 0.015 (0.008-0.026) | 0.014 (0.004-0.036) |
| c.383 T > C (Met128Thr) | Exon 5 | 4/398‡ | 3/147§ | 0.005 (0.002-0.013) | 0.010 (0.002-0.031) |
| c.559 G > A (Val187Ile) | Exon 6 | 65/800‖ | 3/147§ | 0.041 (0.032-0.052) | 0.010 (0.002-0.031) |
| c.597 C > G (Leu199Leu) | Exon 6 | 0/47** | 2/47** | 0 (0-0.048) | 0.021 (0.001-0.080) |

*Data were from 47 specimens obtained from a tissue typing laboratory and screened by heteroduplex analysis (primers L12 and R11). The "C" allele is more common than the "A" allele (frequencies, 0.80 and 0.20). Allele frequencies were estimated from heteroduplex analysis data, rather than from sequencing or allele-specific PCR data.
†Data were from 47 specimens obtained from the tissue typing laboratory and screened by heteroduplex analysis (primers L6 and R6). The allele frequencies were estimated from the heteroduplex analysis data, rather than sequencing or allele-specific PCR on all of the specimens.
‡Data were from 47 specimens obtained from the tissue typing laboratory and screened by heteroduplex analysis and 351 specimens genotyped by allele-specific PCR (50 from the tissue typing laboratory; 82 from a study of genetic variants of prostaglandin metabolism; 219 controls from epidemiologic studies).
§Data were from 147 specimens obtained from the tissue typing laboratory. Forty-seven were screened by heteroduplex analysis, and 100 were genotyped by allele-specific PCR.
‖Data were from the 398 specimens listed in footnote § and 402 control specimens obtained from epidemiologic studies and genotyped by allele-specific PCR.
**Data were from 47 specimens obtained from the tissue typing laboratory and screened by heteroduplex analysis. The two c.597 C > G mutations occurred in specimens that also contained c.559 G > A mutations, confirmed by DNA sequencing.

e. Genotyping by Use of Allele-Specific PCR to Confirm DNA Sequences of H-PGDS Variants and Assess their Frequencies Dried blood spots on blotter paper were used for genotyping (No. 903 paper; Whatman Schleicher and Schuell). The blotter papers were labeled with a code number, but no other identifier. One mm punches of dried blood were tested in duplicate for the three variants, by use of allele-specific PCR. PCR primers for genotyping were: for Ile91Val, L16 and 271AR3, L16 and 271GR3; for Met128Thr, 383TL2 and R13, 383CL2 and R13; for Val187Ile, V187GL and R14, V187AL and R14 (see Table 4). The Val187Ile variant was not found among Chinese (from Hong Kong), Hispanics, Asian Indians, Japanese, Koreans, or Samoans (24-25 individuals each). FIGS. 2A-2C show examples of H-PGDS genotyping by use of allele-specific PCR. The prevalence of the Val187Ile variant was roughly 8% (or 65/800) among African Americans and 2% (or 3/147) among whites (see heterozygote frequencies; Table 5).

f. H-PGDS Expression Vectors and Mutagenesis

A human H-PGDS coding fragment was prepared by use of PCR primers designed from the known coding sequence. Human spleen cDNA (Clontech; Mountain View, Calif.) was the PCR template. PCR primers were: 5'-TAT ACA TAT GCC AAA CTA CAA ACT CAC T-3' (HPGDS-L14B) and 5'-TAT AGG ATC CCT AGA GTT TGG TTT GGG G-3' (HPGDS-R12). Primer L14B contained an NdeI restriction site (CATATG) and a total of 21 nucleotides of the H-PGDS sequence, beginning with the ATG start site. Primer R12 contained 18 nucleotides of H-PGDS (up to and including the TAG stop codon), followed by a BamHI restriction site (GGATCC). The PCR product was subcloned between the NdeI and BamHI restriction sites in the bacterial expression plasmid, pET-5a (Novagen EMD Biosciences; San Diego, Calif.), and the desired sequence of the resulting plasmid was verified. The Ile91Val, Met128Thr, and Val187Ile variants were introduced into the coding sequence by site-directed mutagenesis (QuikChange site-directed mutagenesis kit; Stratagene; La Jolla, Calif.). The mutagenic oligonucleotides were: 5'-GGA ACA ATG TCA TGT TGA TGC TGT TGT GGA CAC TCT GG-3' and 5'-CCA GAG TGT CCA CAA CAG CAT CAA CAT GAC ATT GTT CC-3' (for Ile91Val); 5'-GCT CAC GTA TAA TGC GCC TCA TCT TAC GCA AGA CTT GG-3' and 5'-CCA AGT CTT GCG TAA GAT GAG GCG CAT TAT ACG TGA GC-3' (for Met128Thr); 5'-CCA AGC CAT TCC TGC CAT CGC TAA CTG GAT AAA ACG-3' and 5'-CGT TTT ATC CAG TTA GCG ATG GCA GGA ATG GCT TGG-3' (for Val187Ile). Presence of the variant and absence of PCR artifacts were verified by DNA sequencing.

g. Bacterial Production of H-PGDS

H-PGDS variants were produced in E. coli strain BL21 (DE3; Stratagene). Cells were grown at 37° C. in L-broth medium with ampicillin (150 µg/ml) to an absorbance of 0.7 at 600 nm and then induced with isopropyl β-D-1-thiogalactopyranoside (IPTG; 1 mM) for 4 more hours. Cells were suspended in buffer 1 [phosphate buffered saline (PBS) with 5 mM dithiothreitol (DTT)] and lysed with lysozyme (0.5 mg/ml) while stifling for 30 minutes at 4° C. Soluble protein was recovered by centrifugation (12,000 rpm in a GSA rotor at 4° C.). Ammonium sulfate was added to a concentration of 60% saturation. Pellets were resuspended in buffer 2 (PBS with 5 mM DTT and 5 mM $MgCl_2$) and then loaded directly onto a Sephadex G-75 column (GE Healthcare Biosciences; Piscataway, N.J.). Peak fractions containing H-PGDS were pooled and loaded onto a glutathione-agarose column (Sigma; St. Louis, Mo.), washed with three column volumes of buffer 2 and eluted with two column volumes of freshly prepared buffer 3 (50 mM Tris-Cl pH 9.0 with 10 mM glutathione). Aliquots of the eluted fractions were stored at −80° C. until needed.

h. Specific Activity of H-PGDS Variants

Glutathione transferase activity of H-PGDS enzymes was measured by use of 1-chloro-2,4-dinitrobenzene (CDNB) as substrate. Reactions contained 100 mM potassium phosphate (pH 6.5), 1 mM CDNB, 1 mM reduced glutathione, and 1.8

µg of H-PGDS enzyme in a 300 µl total reaction volume in a quartz cuvette at room temperature. The change in absorbance at 340 nm was monitored during the course of the reaction. The specific activities of each H-PGDS variant (µmol of product per minute per mg of protein) were obtained by averaging three independent measurements. Wild-type and variant H-PGDS enzymes had similar specific activities, in the range of 3-6 µmol/min/mg of protein (Table 1).

i. Thermal Stability of H-PGDS Variant Enzymes

To assess thermal stability, glutathione transferase activities toward CDNB of variant and wild-type enzymes were measured following incubation at 50° C. for 0, 2.5, 5, 7.5, 10, 15, 20, 30, 40, 50, and 60 minutes. All measurements were done in triplicate. The data were assessed statistically by use of analysis of variance with Dunnett's method, comparing the three different enzyme variants to the wild-type. Thermal stability at 50° C. for the Val187Ile variant was increased to roughly 42 minutes, compared to 9 minutes for the wild-type (Table 1 and FIG. 1).

Specific embodiments are discussed in the preceding detailed description. It will, however, be evident that various modifications and changes may be made thereto without departing from the broader spirit and scope of the claims. For example, FIGS. 4A-4C and 8A-8C demonstrate the chemopreventive effects of elevated PGD2 levels on intestinal tumors. The benefits of elevated $PGD_2$ levels are expected to produce similar chemopreventive results in humans. Further, chemoprevention is also anticipated for cancers other than colon cancer, particularly cancer that may be promoted by $PGE_2$ or inhibited by elevated levels of $PGD_2$. The specifications and drawings are, accordingly, to be regarded in an illustrative rather than in a restrictive sense.

---

What is claimed is:

1. A method to inhibit growth of intestinal tumors comprising:
   introducing a composition to a mammal, the composition comprising an effective amount of a first treatment agent comprising a hematopoietic prostaglandin D synthase Val187Ile variant to produce prostaglandin $D_2$ in the mammal and at least one of a second agent in an amount to reduce vasodilation related to increased levels of prostaglandin $D_2$ or to reduce the production of undesirable prostaglandins by reducing transcription of a gene for a microsomal prostaglandin E synthase 1 (mPGES-1) or inhibiting the mPGES-1 enzyme.

2. The method of claim 1, wherein the first treatment agent is one of a prostaglandin D synthase enzyme, a metabolite, or a biochemical product thereof.

3. The method of claim 1, wherein the hematopoietic prostaglandin D synthase Val187Ile variant comprises a genetically engineered form of human hematopoietic prostaglandin D synthase (H-PGDS) wherein a deoxyribonucleic acid (DNA) sequence of an H-PGDS gene, a ribonucleic acid sequence of an H-PGDS transcription product, or an amino acid sequence of an H-PGDS enzyme or protein results in substitution of amino acid valine by isoleucine at position 187 of the enzyme.

4. The method of claim 1, wherein the first treatment agent increases a level or catalytic activity of a prostaglandin D synthase enzyme in the mammal.

5. The method of claim 1, wherein the undesirable prostaglandins comprise prostaglandin $E_2$.

6. The method of claim 1, wherein the second treatment agent is at least one of diferuloylmethane or MK-886.

7. The method of claim 1, wherein the composition further comprises an effective amount of niacin.

8. The method of claim 7, wherein the effective amount of niacin comprises three grams or less per day administered orally.

\* \* \* \* \*